US012127309B2

(12) United States Patent
Nardo et al.

(10) Patent No.: US 12,127,309 B2
(45) Date of Patent: Oct. 22, 2024

(54) PTC HEATING ELEMENT AND WARMING DEVICE INCLUDING SAME FOR USE IN A PATIENT WARMING SYSTEM

(71) Applicant: American Sterilizer Company, Mentor, OH (US)

(72) Inventors: Richard P. Nardo, Highland Heights, OH (US); Andrew Moss, Solon, OH (US); John Michael Kasunich, Mayfield Heights, OH (US); Breese John Watson, Rocky River, OH (US); Hugo van der Walt, Willoughby, OH (US); Farhad Haghgoeian, Solon, OH (US)

(73) Assignee: American Sterilizer Company, Mentor, OH (US)

( * ) Notice: Subject to any disclaimer, the term of this patent is extended or adjusted under 35 U.S.C. 154(b) by 939 days.

(21) Appl. No.: 17/162,298

(22) Filed: Jan. 29, 2021

(65) Prior Publication Data

US 2021/0243843 A1 Aug. 5, 2021

Related U.S. Application Data

(60) Provisional application No. 62/968,612, filed on Jan. 31, 2020.

(51) Int. Cl.
*H05B 1/02* (2006.01)
*H05B 3/03* (2006.01)
(Continued)

(52) U.S. Cl.
CPC ............ *H05B 1/0294* (2013.01); *H05B 3/03* (2013.01); *H05B 3/145* (2013.01); *H05B 3/16* (2013.01); *H05B 3/34* (2013.01); *H05B 2203/02* (2013.01)

(58) Field of Classification Search
CPC .......... A61F 7/0097; A61F 7/08; A61F 7/007; A61F 2007/0244; A61F 2007/0249;
(Continued)

(56) References Cited

U.S. PATENT DOCUMENTS 2,473,183 A 6/1949 Watson
2,512,559 A 6/1950 Williams
(Continued)

FOREIGN PATENT DOCUMENTS

CA 2136066 A1 11/1993
EP 2408407 B1 1/2012
(Continued)

OTHER PUBLICATIONS

International Preliminary Report on Patentability for related International Application No. PCT/US2021/015707 mailed Aug. 11, 2022.
(Continued)

*Primary Examiner* — Eric S Stapleton
(74) *Attorney, Agent, or Firm* — Renner, Otto, Boisselle & Sklar, LLP

(57) ABSTRACT

A heating element includes an electrically insulating layer; resistive layer formed of a positive temperature coefficient material; and an electrically conductive layer disposed between the electrically insulating layer and the resistive layer and including a first bus and a second bus that is spaced apart from the first bus, the resistive layer electrically connecting the first bus and the second bus. The electrically insulating layer, the electrically conductive layer, and the resistive layer are stacked to form a lamination and the lamination having a thickness and a width and length extending orthogonal to the thickness. The lamination may have slits extending through the thickness thereof and along a portion of the length thereof. Terminals may be connected
(Continued)

to the buses and arranged to provide a counter current flow pattern across the lamination. The lamination may be used in a warming device and in connection with a patient warming system.

17 Claims, 17 Drawing Sheets

(51) Int. Cl.
*H05B 3/14* (2006.01)
*H05B 3/16* (2006.01)
*H05B 3/34* (2006.01)

(58) Field of Classification Search
CPC ..... A61F 2007/0074; A61F 2007/0073; H05B 3/03; H05B 3/34; H05B 1/0294; H05B 3/145; H05B 3/16; H05B 2203/02
USPC .......................................................... 219/464
See application file for complete search history.

(56) References Cited

U.S. PATENT DOCUMENTS

| | | | |
|---|---|---|---|
| 3,900,654 A | 8/1975 | Stinger | |
| 4,061,898 A | 12/1977 | Murray et al. | |
| 4,479,795 A | 10/1984 | Mustacich et al. | |
| 4,534,886 A | 8/1985 | Kraus et al. | |
| 4,719,335 A * | 1/1988 | Batliwalla | H05B 3/06 |
| | | | 219/528 |
| 4,761,541 A * | 8/1988 | Batliwalla | H01C 7/027 |
| | | | 219/528 |
| 4,777,351 A * | 10/1988 | Batliwalla | H05B 3/146 |
| | | | 219/541 |
| 4,845,343 A * | 7/1989 | Aune | H05B 3/342 |
| | | | 219/545 |
| 5,008,515 A | 4/1991 | McCormack | |
| 5,125,238 A | 6/1992 | Ragan et al. | |
| 5,422,462 A * | 6/1995 | Kishimoto | H05B 1/0272 |
| | | | 219/545 |
| 5,643,480 A | 7/1997 | Gustavsson et al. | |
| 5,824,996 A * | 10/1998 | Kochman | A41D 13/0051 |
| | | | 338/211 |
| 6,073,284 A | 6/2000 | Borders | |
| 6,078,026 A | 6/2000 | West | |
| 6,093,910 A | 7/2000 | McClintock et al. | |
| 6,149,674 A | 11/2000 | Borders | |
| 6,172,344 B1 | 1/2001 | Gordon et al. | |
| 6,194,692 B1 | 2/2001 | Oberle | |
| 6,229,123 B1 * | 5/2001 | Kochman | H05B 3/58 |
| | | | 219/549 |
| 6,235,049 B1 | 5/2001 | Nazerian | |
| 6,331,695 B1 | 12/2001 | West | |
| 6,346,189 B1 | 2/2002 | Dai et al. | |
| 6,403,935 B2 * | 6/2002 | Kochman | H05B 3/58 |
| | | | 219/545 |
| 6,483,087 B2 | 11/2002 | Gardner et al. | |
| 6,541,744 B2 | 4/2003 | Von Arx et al. | |
| 6,581,400 B2 | 6/2003 | Augustine et al. | |
| 6,582,456 B1 | 6/2003 | Hand et al. | |
| 6,653,607 B2 | 11/2003 | Ellis et al. | |
| 6,664,512 B2 | 12/2003 | Horey et al. | |
| 6,703,845 B2 | 3/2004 | Stanley et al. | |
| 6,706,402 B2 | 3/2004 | Rueckes et al. | |
| 6,781,166 B2 | 8/2004 | Lieber et al. | |
| 6,803,543 B2 | 10/2004 | Argersinger et al. | |
| 6,814,889 B1 | 11/2004 | O'Grady et al. | |
| 6,919,592 B2 | 7/2005 | Segal et al. | |
| 6,924,467 B2 | 8/2005 | Ellis et al. | |
| 6,933,409 B1 | 8/2005 | Poojary et al. | |
| 6,933,469 B2 | 8/2005 | Ellis et al. | |
| 6,967,309 B2 | 11/2005 | Wyatt et al. | |
| 6,974,935 B2 | 12/2005 | O'Grady | |
| 7,001,416 B2 | 2/2006 | Augustine et al. | |
| 7,022,950 B2 | 4/2006 | Haas et al. | |
| 7,053,344 B1 | 5/2006 | Surjan et al. | |
| 7,060,241 B2 | 6/2006 | Glatkowski | |
| 7,176,419 B2 | 2/2007 | Ellis et al. | |
| 7,191,482 B2 | 3/2007 | Romano et al. | |
| 7,196,289 B2 | 3/2007 | Ellis et al. | |
| 7,202,443 B2 | 4/2007 | Rock et al. | |
| 7,211,772 B2 | 5/2007 | Carpino, II et al. | |
| 7,372,006 B2 | 5/2008 | Aisenbrey | |
| 7,416,699 B2 | 8/2008 | Dai et al. | |
| 7,468,332 B2 | 12/2008 | Avioni | |
| 7,543,344 B2 | 6/2009 | Augustine et al. | |
| 7,663,076 B2 | 2/2010 | Tarry | |
| 7,714,255 B2 | 5/2010 | Augustine et al. | |
| 7,745,810 B2 | 6/2010 | Rueckes et al. | |
| 7,786,408 B2 | 8/2010 | Augustine et al. | |
| 7,851,729 B2 | 12/2010 | Augustine et al. | |
| 8,016,779 B2 | 9/2011 | Brown et al. | |
| 8,062,343 B2 | 11/2011 | Augustine et al. | |
| 8,153,940 B2 | 4/2012 | Niemz et al. | |
| 8,283,602 B2 | 10/2012 | Augustine et al. | |
| 8,581,158 B2 | 11/2013 | Heintz et al. | |
| 8,624,164 B2 | 1/2014 | Deibel et al. | |
| 8,772,676 B2 | 7/2014 | Augustine et al. | |
| 9,191,997 B2 | 11/2015 | Weib | |
| 9,468,045 B2 | 10/2016 | Zhang et al. | |
| 9,642,404 B2 | 5/2017 | Giles et al. | |
| 9,687,093 B2 | 6/2017 | Giles et al. | |
| 9,693,891 B2 | 7/2017 | MacIntyre-Ellis et al. | |
| 2001/0025846 A1 * | 10/2001 | Kochman | H05B 3/34 |
| | | | 219/545 |
| 2002/0019654 A1 | 2/2002 | Ellis et al. | |
| 2003/0189037 A1 * | 10/2003 | Kochman | H05B 3/58 |
| | | | 219/549 |
| 2004/0100131 A1 * | 5/2004 | Howick | B60N 2/002 |
| | | | 297/180.12 |
| 2004/0173028 A1 | 9/2004 | Rix | |
| 2005/0187527 A1 | 8/2005 | Rix | |
| 2005/0242081 A1 * | 11/2005 | Howick | B60N 2/5685 |
| | | | 219/529 |
| 2006/0052852 A1 | 3/2006 | Wyatt et al. | |
| 2006/0062815 A1 | 3/2006 | Djie | |
| 2006/0180583 A1 * | 8/2006 | Jones | H05B 1/0236 |
| | | | 219/202 |
| 2007/0016271 A1 * | 1/2007 | Hammond | A61F 7/007 |
| | | | 607/96 |
| 2007/0068923 A1 * | 3/2007 | Augustine | A61F 7/007 |
| | | | 219/465.1 |
| 2008/0083720 A1 * | 4/2008 | Gentile | A43B 3/35 |
| | | | 219/211 |
| 2008/0083721 A1 * | 4/2008 | Kaiserman | H05B 3/342 |
| | | | 219/211 |
| 2008/0083740 A1 * | 4/2008 | Kaiserman | A43B 3/35 |
| | | | 219/520 |
| 2008/0223841 A1 * | 9/2008 | Lofy | B60N 2/5678 |
| | | | 219/202 |
| 2008/0249447 A1 | 10/2008 | Brown et al. | |
| 2008/0255538 A1 | 10/2008 | Ellis | |
| 2008/0255641 A1 | 10/2008 | Ellis | |
| 2010/0213189 A1 * | 8/2010 | Keite-Telgenbuescher | |
| | | | H05B 3/845 |
| | | | 219/548 |
| 2011/0226751 A1 | 9/2011 | Lazanja et al. | |
| 2011/0274418 A1 * | 11/2011 | Meisiek | F16L 53/38 |
| | | | 392/480 |
| 2012/0013433 A1 * | 1/2012 | Rauh | H01C 13/00 |
| | | | 174/128.1 |
| 2013/0060308 A1 | 3/2013 | Ellis | |
| 2013/0073012 A1 | 3/2013 | Ellis | |
| 2013/0186884 A1 | 7/2013 | Barfuss et al. | |
| 2013/0237983 A1 | 9/2013 | Giles et al. | |
| 2014/0127566 A1 * | 5/2014 | Kuriki | H01M 4/366 |
| | | | 429/211 |
| 2014/0261447 A1 | 9/2014 | Giles | |
| 2014/0277306 A1 | 9/2014 | Giles | |
| 2015/0290027 A1 | 10/2015 | Augustine et al. | |
| 2015/0327332 A1 | 11/2015 | Augustine et al. | |
| 2015/0366367 A1 | 12/2015 | Augustine et al. | |

(56) References Cited

U.S. PATENT DOCUMENTS

| | | |
|---|---|---|
| 2015/0373781 A1 | 12/2015 | Augustine et al. |
| 2016/0081846 A1 | 3/2016 | Katzenstein |
| 2016/0143091 A1 | 5/2016 | Augustine et al. |
| 2017/0209305 A1 | 7/2017 | Kaforey et al. |
| 2017/0231811 A1 | 8/2017 | Cubon |
| 2017/0298567 A1 | 10/2017 | Abula |

FOREIGN PATENT DOCUMENTS

| | | |
|---|---|---|
| WO | 03011128 A1 | 2/2003 |
| WO | 2003088881 A2 | 10/2003 |
| WO | 2006131785 A2 | 12/2006 |
| WO | 2010086740 A1 | 8/2010 |
| WO | 2011084957 A1 | 7/2011 |
| WO | 2013134477 A1 | 9/2013 |
| WO | 2014152227 A1 | 9/2014 |
| WO | 2016113633 A1 | 7/2016 |
| WO | 2017068416 A1 | 4/2017 |
| WO | 2017216631 A2 | 12/2017 |

OTHER PUBLICATIONS

PCT/US2021/015707; PCT International Search Report and Written Opinion of the International Searching Authority mailed May 10, 2021.

\* cited by examiner

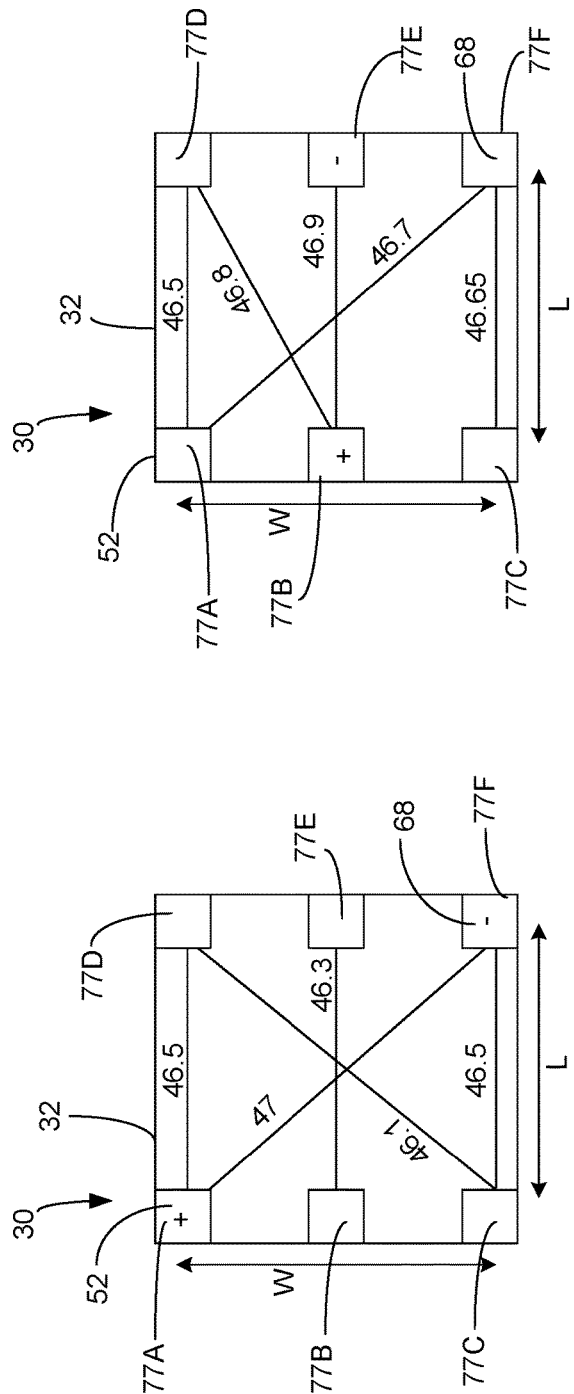
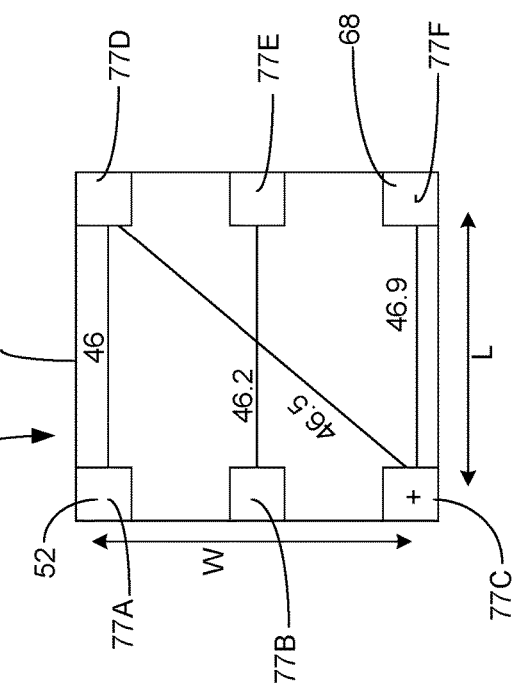

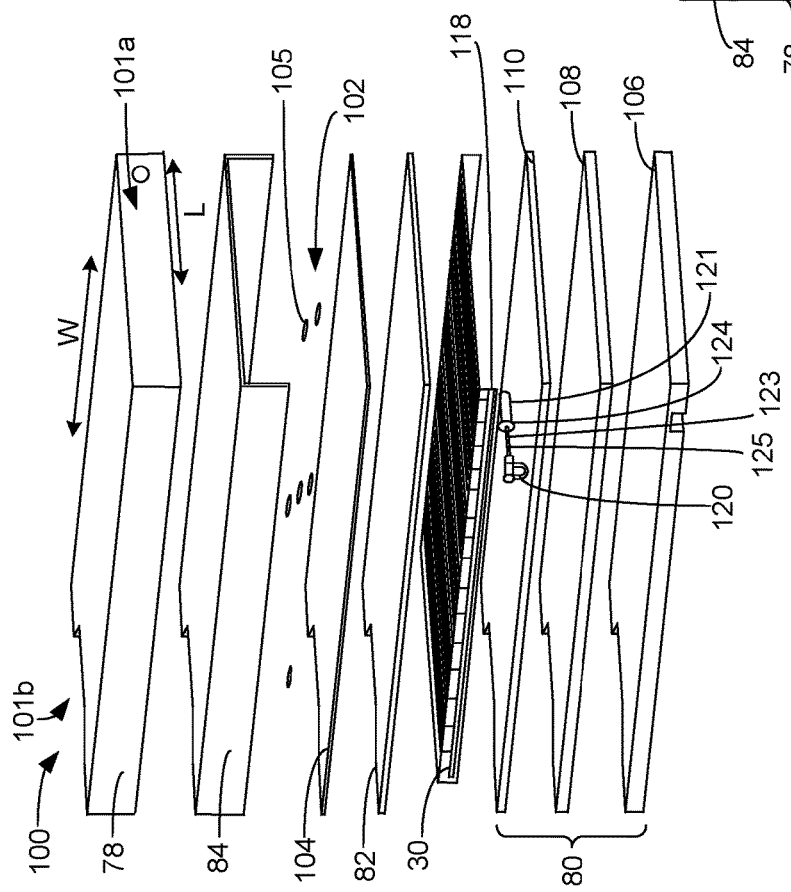
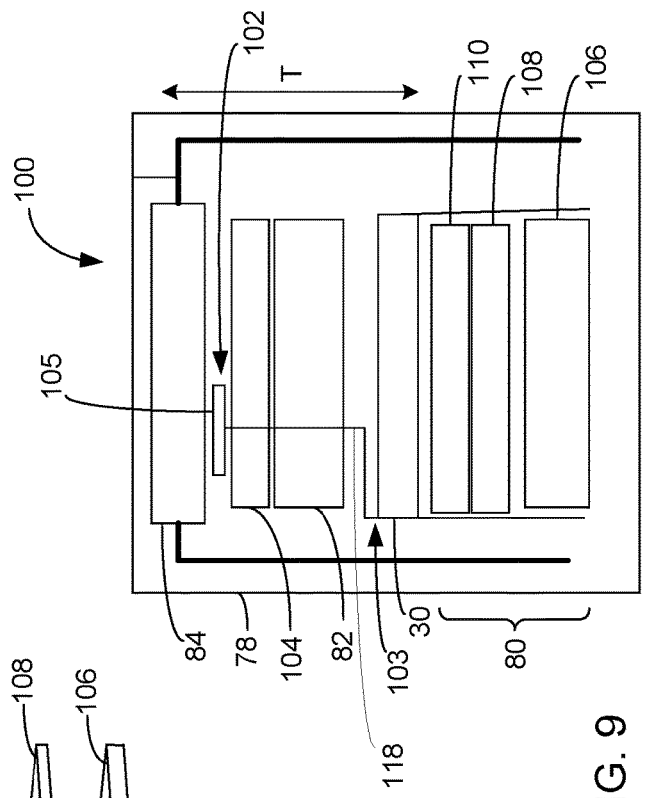
FIG. 8
FIG. 9

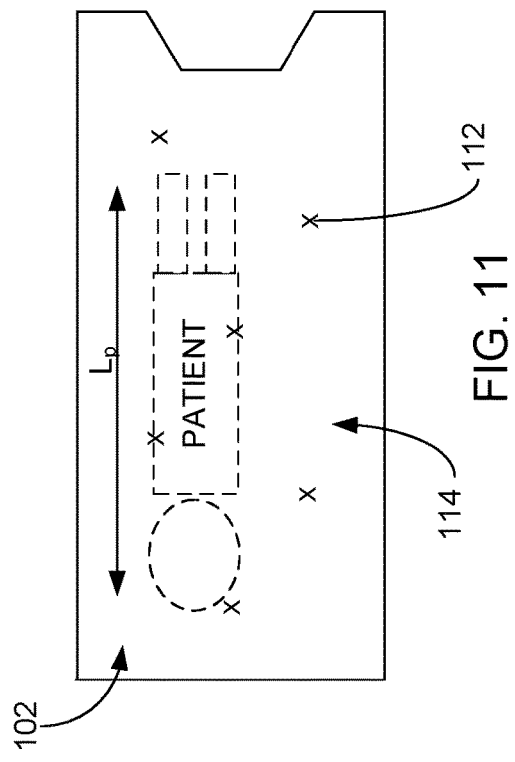
FIG. 10
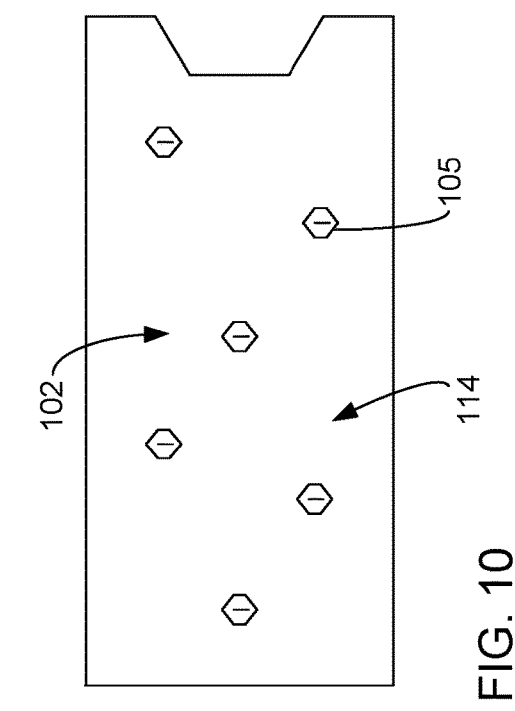
FIG. 11
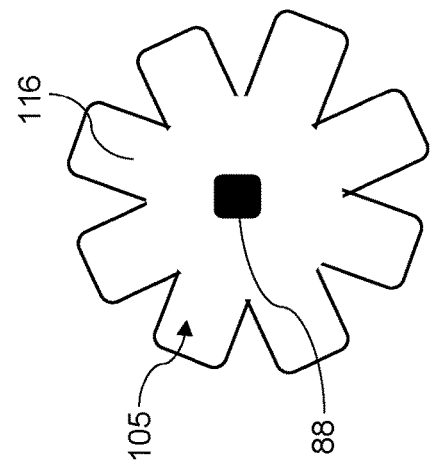
FIG. 12B
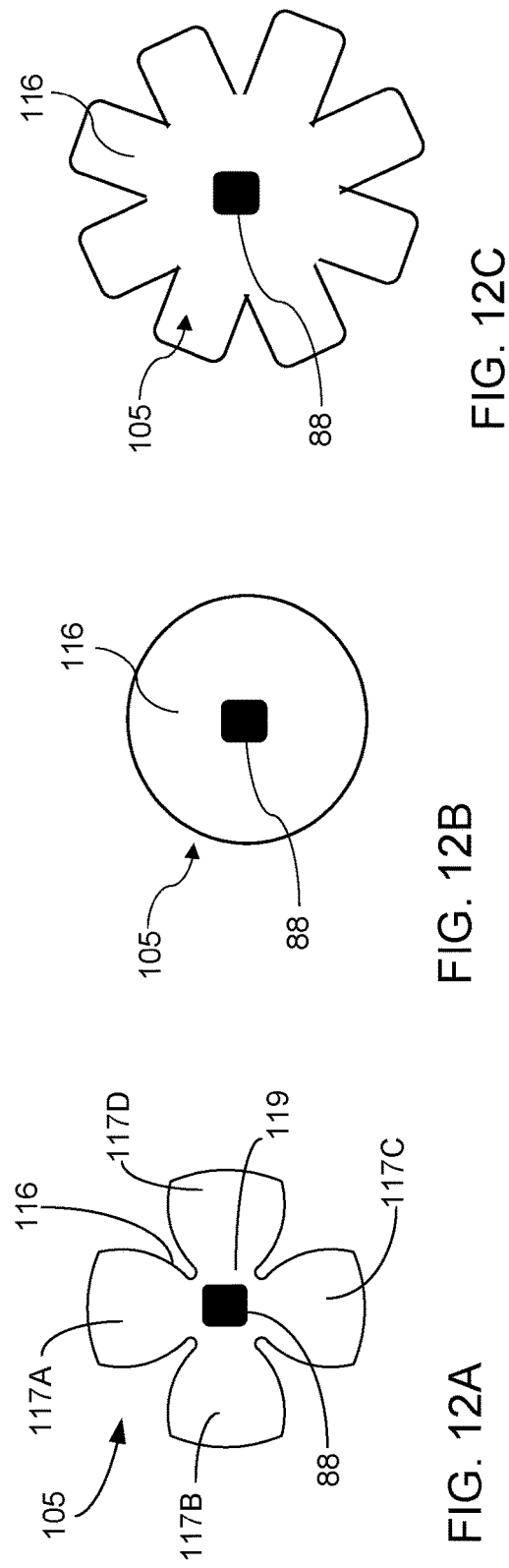
FIG. 12A
FIG. 12C

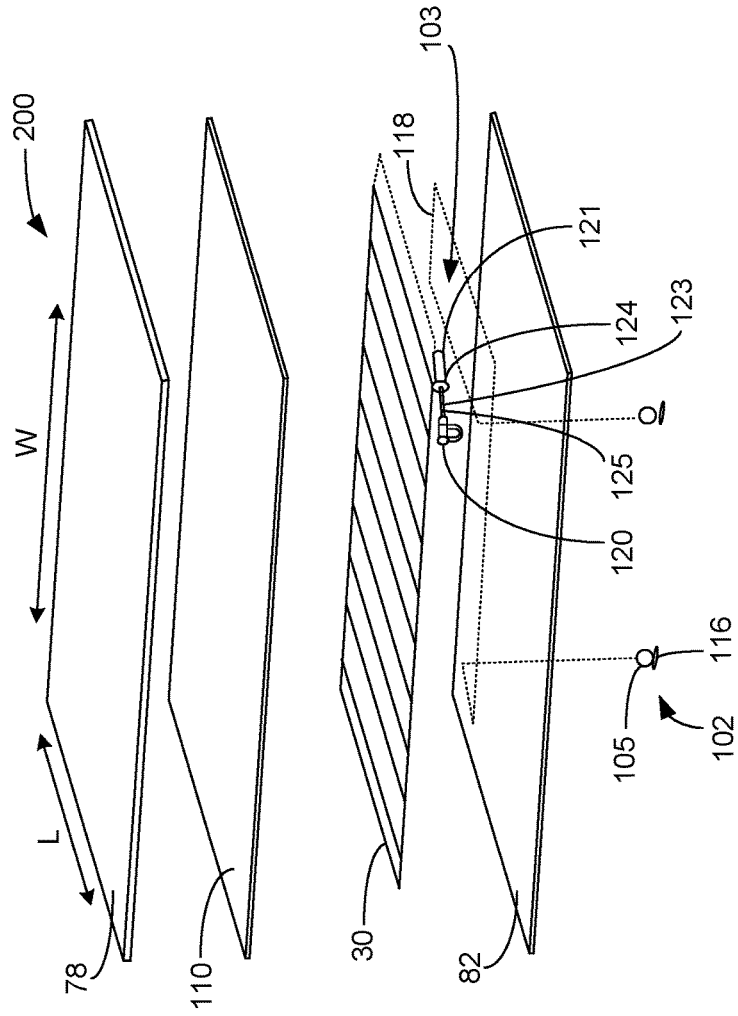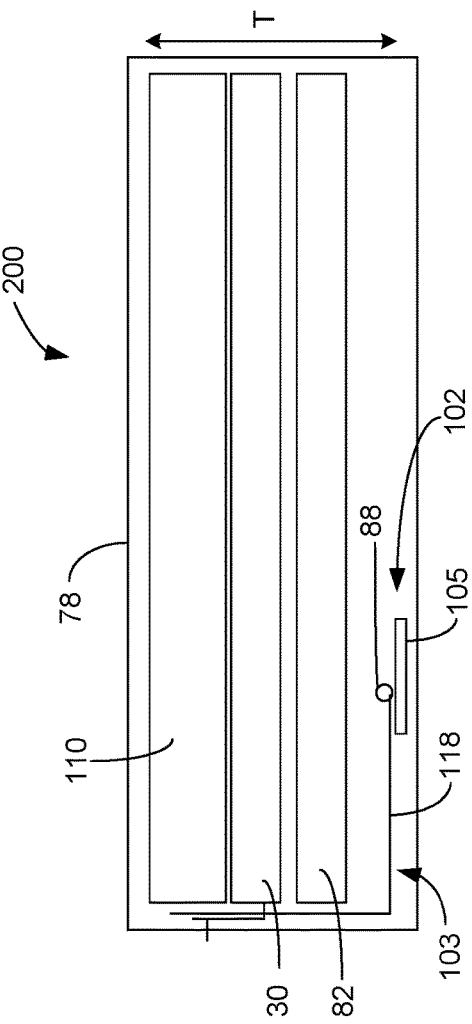

PTC HEATING ELEMENT AND WARMING DEVICE INCLUDING SAME FOR USE IN A PATIENT WARMING SYSTEM

This application claims priority to U.S. Patent Application No. 62/968,612 filed Jan. 31, 2020. This prior application is incorporated herein by reference.

FIELD OF THE INVENTION

The technology of the present disclosure relates generally to patient warming systems, and more particularly to positive temperature coefficient (PTC) heating elements and warming devices usable in a patient warming system for warming a patient.

BACKGROUND

Patient warming devices are used in various medical applications. For example, surgical patients that undergo surgery and require anesthesia may be warmed using a warming device, as they may be unable to regulate their core body temperature. The patients may be subject to detrimental heat loss if their core body temperature is not able to be maintained.

One conventional method of warming patients includes using forced air convective warming. However, forced air convective warming systems are disadvantageous for several reasons. Using convective warming may transmit lower thermal energy as compared with conductive warming systems and convective airflow may cause surgical site contamination. Still other disadvantages include less temperature control being available at the patient contact surface, inconsistent temperatures at the surface of the warming device, excessive noise of the system due to a fan, and the increased surgical site temperature for the surgeons. Forced air convective warming systems also cannot be used during patient preparation due to contamination concerns from the airflow.

Another conventional method of warming patients includes using fluid conductive warming. However, similar to forced air convective warming systems, fluid conductive warming systems have been found to be unable to provide temperature consistency across the blanket for the patient, and can be excessively noisy due to the fan. The temperature at the patient contact surface may also be difficult to control using fluid conductive warming systems. Leaks in the fluid conductive warming system are also a concern. Fluid conductive warming systems may also provide challenges in that a fan on the heat exchanger of the system may build up contaminants that are subsequently blown around, resulting in infection.

Patient warming systems have been implemented in which electrically conductive warming is utilized. However, control of electrically conductive warming systems is also an issue both in terms of temperature uniformity and safety.

SUMMARY OF INVENTION

The present disclosure, therefore, relates to a heating element including a resistive layer formed of a positive temperature coefficient (PTC) material (e.g., ink). Using the PTC material provides a self-regulating characteristic for the heating element such that as the heating element is heated, the electrical resistance of the PTC material in the heating element increases to limit the flow of current through the heating element. The heating element may be included in a warming device such as an underbody pad (e.g., torso pad), over-body blanket, under-body blanket, headrest, and the like. The warming device may be used in a patient warming system for warming a patient.

In accordance with an aspect of the disclosure, a heating element includes: an electrically insulating layer; a resistive layer formed of a positive temperature coefficient material; and an electrically conductive layer disposed between the electrically insulating layer and the resistive layer and including a first bus and a second bus that is spaced apart from the first bus, the resistive layer electrically connecting the first bus and the second bus, wherein the electrically insulating layer, the electrically conductive layer, and the resistive layer are stacked to form a lamination and the lamination having a thickness and a width and length extending orthogonal to the thickness, and the lamination has a plurality of slits extending through the thickness thereof and along a portion of the length thereof.

In some embodiments, the slits are evenly spaced along the width of the lamination.

In some embodiments, the slits segment the lamination into parallel strips that each have a width that is less than a length thereof.

In some embodiments, each of the parallel strips have the same width and the same length.

In some embodiments, the slits extend along more than half the length of the lamination.

In some embodiments, the first bus includes a first bus base extending along a first side of the lamination in the width direction and the second bus includes a second bus base extending along a second side of the lamination opposite the first side in the width direction, wherein the first bus includes first fingers that extend from the first bus base toward the second bus base and the second bus includes second fingers that extend from the second bus base toward the first bus base.

In some embodiments, the slits extend along the length direction.

In some embodiments, the first fingers and the second fingers extend parallel to the slits.

In some embodiments, the heating element further includes a first terminal connected to the first bus base and a second terminal connected to the second bus base, wherein the first terminal and the second terminal are arranged to provide a counter current flow pattern across the lamination.

In some embodiments, the first terminal and the second terminal are diagonally opposed relative to each other across the lamination.

In some embodiments, the lamination further includes a layer arrangement adjacent the resistive layer, the layer arrangement including an additional insulating layer and a fabric layer.

In some embodiments, a warming device includes: the heating element; a spacer layer formed of a fabric material; an insulating foam layer formed of a viscoelastic material; a temperature sensor assembly including a plurality of temperature sensors; and a cover material in which the lamination, the spacer layer, the viscoelastic foam layer, and the temperature sensor assembly are enclosed.

In some embodiments, the temperature sensors are arranged in a predetermined pattern.

In some embodiments, the predetermined pattern is a pattern in which the temperature sensors are evenly spaced or a pattern in which the temperature sensors are unevenly spaced relative to one another.

In some embodiments, each temperature sensor includes one or more thermistors and a heat spreader attached to the one or more thermistors, the heat spreader formed of a graphite material.

In some embodiments, the heat spreader includes a clover leaf shape.

In some embodiments, the warming device further includes a wiring assembly that is configured to provide voltage to the heating element and connects the thermistors to a control system.

In some embodiments, the warming device further includes a grommet engageable against the cover material, wherein the grommet is configured to provide interference between a cord of the wiring assembly and the grommet.

In some embodiments, the material of the spacer layer has a density that is between 48 and 65 kilograms per cubic meter and a thermal conductivity that is between 0.160 and 0.170 Watts per meter per degree Celsius.

In some embodiments, the warming device is an underbody pad further including a base foam layer arrangement arranged adjacent the heating element opposite the spacer layer.

In some embodiments, the warming device further includes an additional spacer layer having a thickness that is less than a thickness of the spacer layer, wherein the spacer layer is arranged adjacent the lamination, the insulating foam layer is arranged adjacent the spacer layer, and the additional spacer layer is arranged adjacent the insulating foam layer opposite the spacer layer.

In some embodiments, the base foam layer arrangement includes a first foam layer, a second foam layer arranged adjacent the first foam layer and having a density that is less than the first foam layer, and a third foam layer arranged adjacent the second foam layer opposite the first foam layer and formed of a viscoelastic material.

In some embodiments, the warming device is a blanket in which the heating element is arranged between the spacer layer and the insulating foam layer.

In accordance with another aspect of the disclosure, a heating element includes: an electrically insulating layer; a resistive layer formed of a positive temperature coefficient material; an electrically conductive layer disposed between the electrically insulating layer and the resistive layer and including a first bus and a second bus that is spaced apart from the first bus, the resistive layer electrically connecting the first bus and the second bus, wherein the electrically insulating layer, the electrically conductive layer, and the resistive layer are stacked to form a lamination and the lamination having a thickness and a width and length extending orthogonal to the thickness; and a first terminal connected to the first bus and a second terminal connected to the second bus for supplying current to the first bus and the second bus, wherein the first terminal and the second terminal are arranged to provide a counter current flow pattern across the lamination.

In some embodiments, the first bus includes a first bus base extending along a first side of the lamination in the width direction and the second bus includes a second bus base extending along a second side of the lamination opposite the first side in the width direction, wherein the first bus includes first fingers that extend from the first bus base toward the second bus base and the second bus includes second fingers that extend from the second bus base toward the first bus base.

In some embodiments, the first terminal and the second terminal are diagonally opposed relative to each other across the lamination.

In some embodiments, a warming device includes: the heating element; a spacer layer formed of a fabric material; an insulating foam layer formed of a viscoelastic material; a temperature sensor assembly including a plurality of temperature sensors; and a cover material in which the lamination, the spacer layer, the viscoelastic foam layer, and the temperature sensor assembly are enclosed.

In some embodiments, the warming device is an underbody pad further includes: a base foam layer arrangement that is arranged adjacent the heating element opposite the spacer layer and includes a plurality of different foam layers; and an additional spacer layer having a thickness that is less than a thickness of the spacer layer, wherein the spacer layer is arranged adjacent the lamination, the insulating foam layer is arranged adjacent the spacer layer, and the additional spacer layer is arranged adjacent the insulating foam layer opposite the spacer layer.

In some embodiments, the warming device is a blanket in which the heating element is arranged between the spacer layer and the insulating foam layer.

In accordance with another aspect of the disclosure, a warming device includes: a heating element, including: an electrically insulating layer; a resistive layer formed of a positive temperature coefficient material; and an electrically conductive layer disposed between the electrically insulating layer and the resistive layer and including a first bus and a second bus that is spaced apart from the first bus, the resistive layer electrically connecting the first bus and the second bus, wherein the electrically insulating layer, the electrically conductive layer, and the resistive layer are stacked to form a lamination and the lamination having a thickness and a width and length extending orthogonal to the thickness; a spacer layer formed of a fabric material; an insulating foam layer formed of a viscoelastic material; a temperature sensor assembly including a plurality of temperature sensors; and a cover material in which the lamination, the spacer layer, the viscoelastic foam layer, and the temperature sensor assembly are enclosed.

In some embodiments, the temperature sensors are arranged in a predetermined pattern.

In some embodiments, each temperature sensor includes one or more thermistors and a heat spreader attached to the one or more thermistors, the heat spreader formed of a graphite material and includes a clover leaf shape.

In some embodiments, the warming device further includes a wiring assembly that is configured to provide voltage to the heating element and connects the temperature sensors to a control system.

In some embodiments, the warming device further includes a grommet engageable against the cover material, wherein the grommet is configured to provide interference between a cord of the wiring assembly and the grommet.

In some embodiments, the material of the spacer layer has a density that is between 48 and 65 kilograms per cubic meter and a thermal conductivity that is between 0.160 and 0.170 Watts per meter per degree Celsius.

In some embodiments, the warming device is an underbody pad further including: a base foam layer arrangement that is arranged adjacent the heating element opposite the spacer layer and includes a plurality of different foam layers; and an additional spacer layer having a thickness that is less than a thickness of the spacer layer, wherein the spacer layer is arranged adjacent the heating element, the insulating foam layer is arranged adjacent the spacer layer, and the additional spacer layer is arranged adjacent the insulating foam layer opposite the spacer layer.

In some embodiments, the warming device is a blanket in which the heating element is arranged between the spacer layer and the insulating foam layer.

In accordance with another aspect of the disclosure, a method of forming a blanket includes: ultrasonically welding a spacer fabric to a cover material with an unsupported urethane tape; attaching a heating element including a positive temperature coefficient material to the spacer fabric using an acrylic adhesive tape; attaching an insulation layer to the spacer fabric using adhesive along a perimeter thereof; attaching a temperature sensor assembly to the spacer fabric using adhesive; and ultrasonically welding one or more seams of the cover to enclose the heating element, the insulation layer, the spacer fabric, and the temperature sensor assembly.

These and further features will be apparent with reference to the following description and attached drawings which set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings. The invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

The annexed drawings, which are not necessarily to scale, show various aspects of the present disclosure.

FIG. 7A is a schematic drawing showing a test setup for measuring voltage in the heating element of FIG. 6.

FIG. 7B is a schematic drawing showing a test setup for measuring voltage in the heating element of FIG. 6.

FIG. 7C is a schematic drawing showing a test setup for measuring voltage in the heating element of FIG. 6.

FIG. 8 is an exploded perspective schematic view of an exemplary underbody pad including the heating element of FIG. 1.

FIG. 9 is a schematic side view of the exemplary underbody pad of FIG. 8.

FIG. 10 is a top view of the exemplary underbody pad of FIG. 8.

FIG. 11 is a schematic drawing showing a patient placed on the underbody pad of FIG. 10 relative to the sensor arrangement.

FIGS. 12A-12C are front views of exemplary heat spreaders.

FIG. 16 is a flowchart showing an exemplary method of manufacturing the underbody pad of FIG. 8.

FIG. 17 is an exploded perspective schematic view of an exemplary blanket including the heating element of FIG. 1.

FIG. 18 is a schematic side view of the exemplary blanket of FIG. 17.

DETAILED DESCRIPTION

Figure 1:
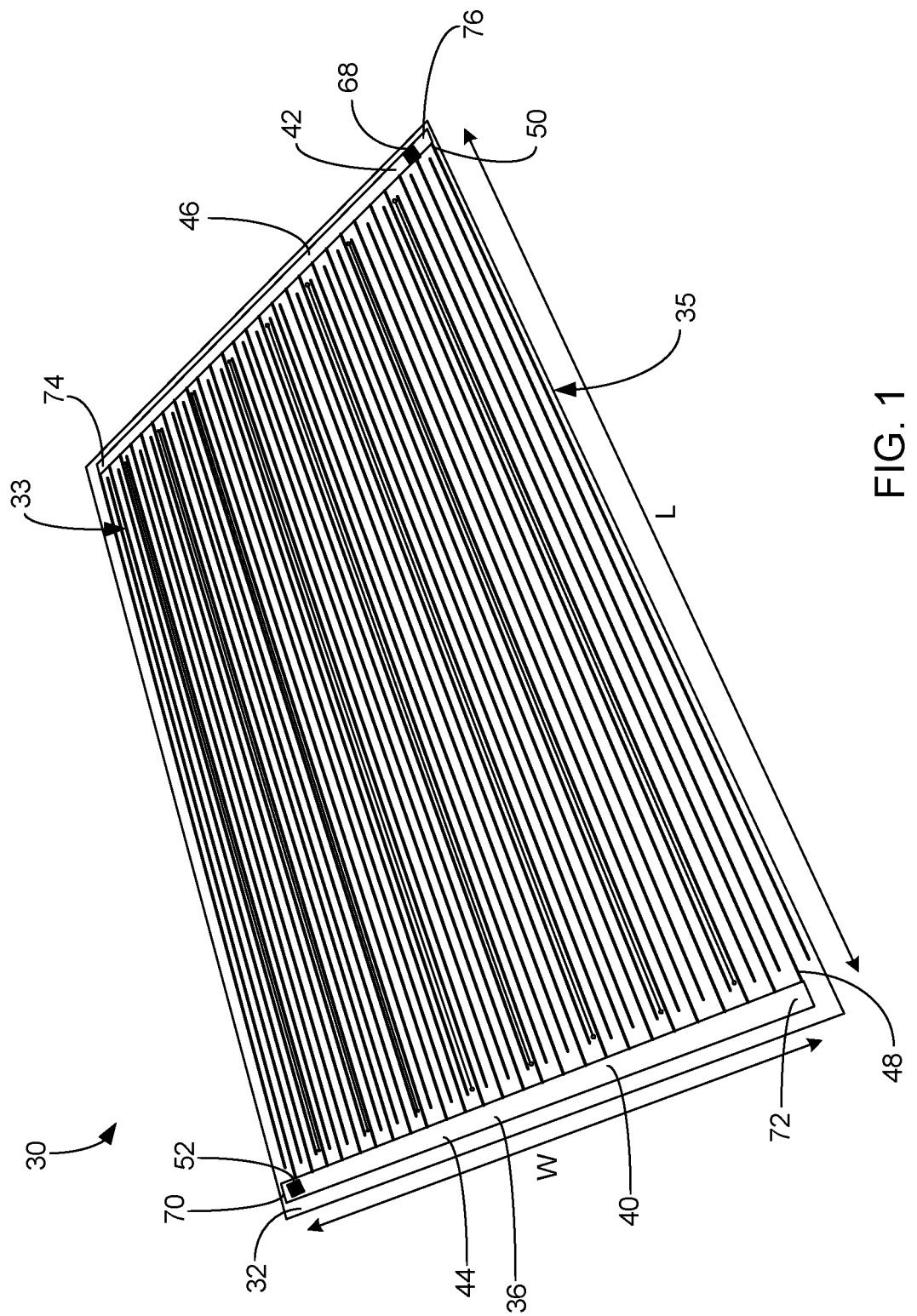
FIG. 1 is a perspective view of a heating element.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. Any alterations and further modifications of the described embodiments, and any further applications of the principles of the present disclosure as described herein, are contemplated as would normally occur to one skilled in the art to which the present disclosure relates.

Figure 2:
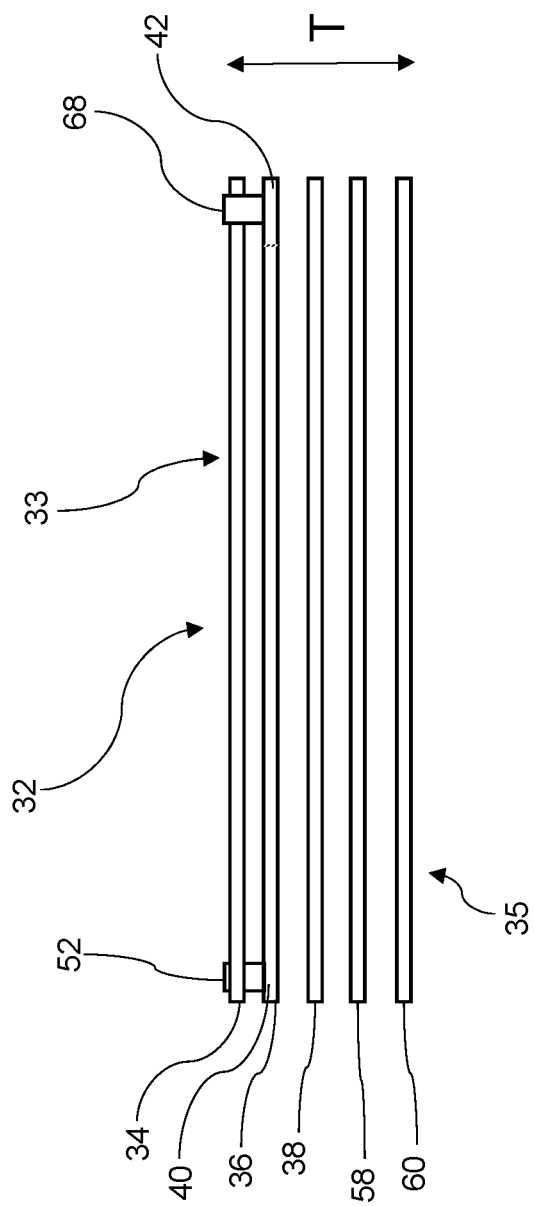
FIG. 2 is a schematic drawing showing an exemplary layer arrangement of the heating element of FIG. 1.

With reference to FIGS. 1 and 2, a heating element is shown at 30. The heating element 30 may be included as part of a warming device, such as an underbody pad, over-body blanket, under-body blanket, headrest, and the like. A warming device including the heating element 30 may be used in a patient warming system.

The heating element 30 includes a plurality of vertically stacked layers that form a lamination 32. The lamination 32 has a thickness T (FIG. 2) and a width W and length L extending orthogonal to the thickness. The lamination 32 includes opposed major surfaces 33, 35 that extend in the width W and length L directions. The lamination 32 may have any suitable shape (e.g., rectangular, circular, polygonal, non-symmetrical shape, etc.). The shape may be dependent on the application or implementation of the heating element 30. For example, FIG. 1 shows an embodiment in which the lamination 32 is rectangular in shape, with the opposed major surfaces 33, 35 of the lamination being rectangular in shape.

FIG. 2 shows an exemplary embodiment of the lamination 32 including at least one layer that provides a self-regulating characteristic for the heating element 30. The lamination 32 includes an electrically insulating layer 34, a resistive layer 38, and an electrically conductive layer 36 disposed between the electrically insulating layer 34 and the resistive layer 38. The electrically insulating layer 34 may constitute a substrate layer of the lamination 32 and may be formed of any suitable insulating and flexible material. Examples of suitable materials for the electrically insulating layer 34 include polyethylene, polyethylene terephthalate (PET), thermoplastic polyurethane (PU), or polyamide. Other plastic materials may be suitable. The electrically insulating layer 34 may have any suitable thickness, such as a thickness that is between 20 and 100 micrometers.

The electrically conductive layer 36 is arranged adjacent the electrically insulating layer 34 and may be formed of a screen-printed conductive ink. In some embodiments, the screen-printed conductive ink is a flexible polymeric ink. In other embodiments, the electrically conductive layer 36 is a metal or metal alloy (e.g., silver, gold, platinum, etc.). The electrically conductive layer 36 may be applied to the electrically insulating layer 34 by screen printing or any other suitable method, such as deposition, digital printing, inkjet printing, flexographic printing, or gravure printing. At least two electrical buses 40, 42 are formed as part of the electrically conductive layer 36 and arranged such that they are spaced relative to each other. A first bus 40 includes a first bus base 44 and a second bus 42 includes a second bus base 46. The bus bases 44, 46 are spaced apart from each other and extend along opposite sides of the lamination 32 (e.g., parallel to one another). Each bus base 44, 46 is elongated along the width W of the lamination 32 The bus bases 44, 46 may extend along most of the entire width W of the lamination. The shape of the bus bases 44, 46 may be rectangular such that the dimension of the respective bus base 44, 46 in the length direction L is much less than the elongated dimension thereof in the width direction W. Other shapes may also be suitable for the bus bases 44, 46.

Each of the busses 40, 42 further includes fingers 48, 50 that extend from the respective bus base 44, 46 toward the other bus base 44, 46. With reference to the exemplary embodiment shown in FIG. 1, fingers 48 extend from bus base 44, and fingers 50 extend from bus base 46. The fingers 48, 50 extend along the length L of the lamination 32 and may be arranged parallel to each other. As shown, the fingers 48 are interdigitated. Each of the fingers 48, 50 may extend along most of the length L of the lamination 32 and may have a dimension in the width direction W that is substantially less than the dimension of the bus bases 44, 46 in the width direction W. In some embodiments, the dimension of each of the fingers in the width direction W is in the range of 0.5 mm to 15 mm. In other embodiments, the dimension of each of the fingers in the width direction W is in the range of 0.5 mm to 10 mm.

The fingers 48, 50 are spaced apart from one another in the width direction W. The spacing between two adjacent fingers 48, 50 may be used to at least in part set the resistance of the heating element. When used in connection with the resistive layer 38, a large spacing between adjacent fingers 48, 50 may contribute to a greater resistance as compared with a lower resistance when a smaller spacing between adjacent fingers 48, 50 is used. In some examples, the spacing between adjacent fingers 48, 50 in the width direction W is in the range of 0.01 mm to 30 mm. In other examples, the spacing between adjacent fingers 48, 50 in the width direction W is in the range of 0.1 mm to 20 mm. In other examples, the spacing between adjacent fingers 48, 50 in the width direction W is in the range of 0.1 mm to 15 mm.

It will be appreciated that while FIG. 1 shows an exemplary bus arrangement provided as part of an exemplary rectangular-shaped lamination, in other embodiments the busses may have other suitable arrangements of bus bases and fingers.

The resistive layer 38 is configured to provide the self-regulating characteristic for the heating element 30. The resistive layer 38 is formed adjacent the electrically conductive layer 36 and is formed of a positive temperature coefficient (PTC) material. In some embodiments, the PTC material is a PTC ink. The PTC material may be printed over the electrically conductive layer 36 for electrically connecting the busses 40, 42. The PTC material has a higher electrical resistance than the electrically conductive layer 36. The PTC material may be selected and/or produced to achieve a predetermined threshold temperature at which the heating element 30 is self-regulating. For example, a temperature between 40° C. and 65° C. may be the threshold temperature for a particular application. In another example, a temperature between 45° C. and 65° C. may be the threshold temperature for a particular application. In yet another example, a temperature between 40° C. and 55° C. may be the threshold temperature for a particular application. In an exemplary application, the threshold temperature may be around 55° C. The "self-regulating" effect is achieved by an increase in resistance to a level at which current either no longer flows or is reduced to an amount at which the heating element no longer increases in temperature. Variation of factors such as the amount and/or type of electrical conductive material provided in the PTC material, and the amount and/or type of carrier material used in the PTC material can affect the performance of the PTC material to achieve a predetermined threshold temperature at which the heating element is self-regulating.

Figure 3A:
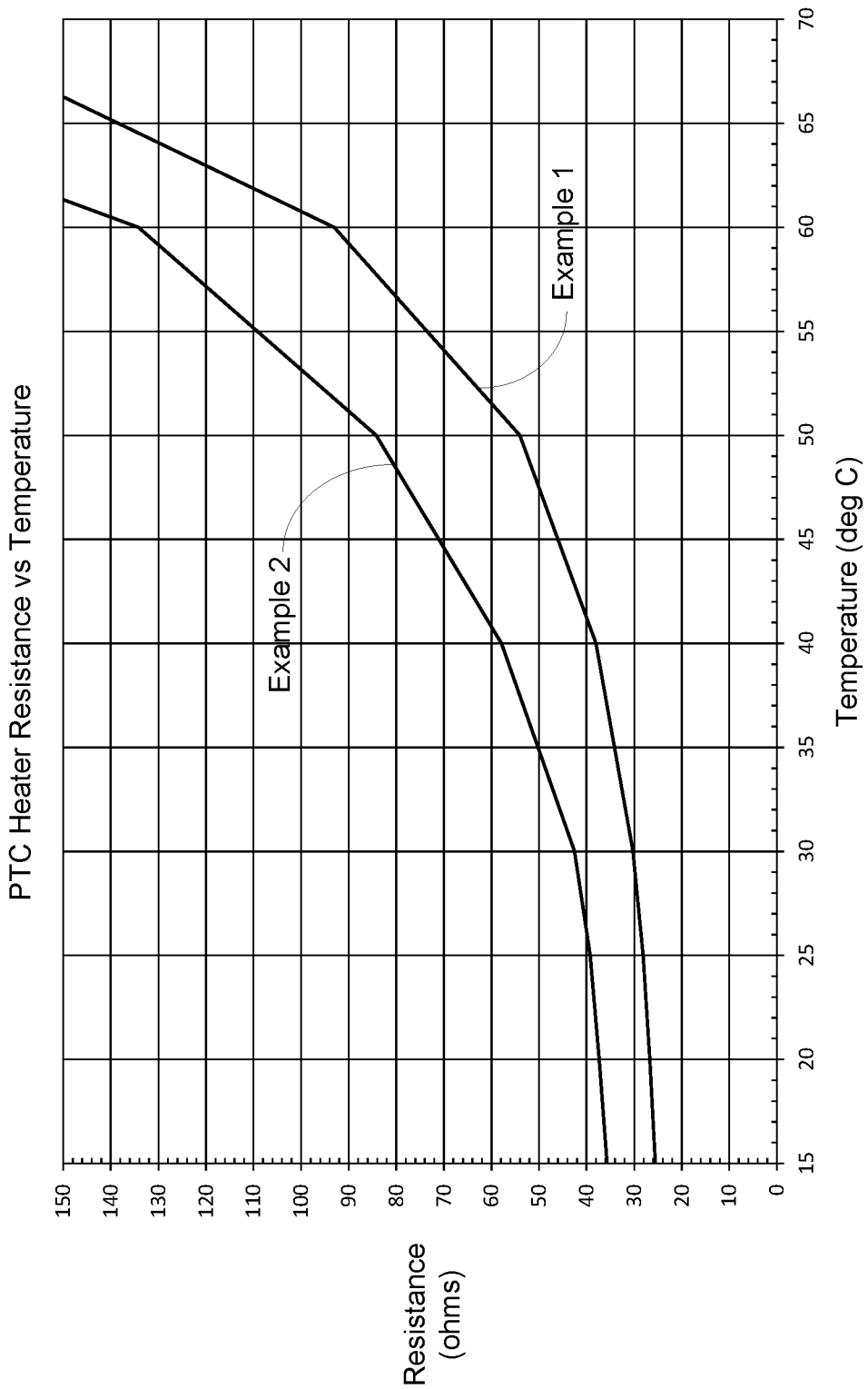
FIGS. 3A and 3B show resistance curves of exemplary heating elements having the configuration of that shown in FIGS. 1 and 2.

FIG. 3A shows resistance curves of respective exemplary heating elements having the configuration of that shown in FIGS. 1 and 2. In the example shown, Example 1 includes a PTC material having more electrical conductive material therein as compared with the PTC material of Example 2. Both curves are parabolic in shape, but at a given temperature, the resistance of the PTC material of Example 2 is higher than the resistance of the PTC material of Example 1. If, for example, a resistance of 80Ω is the resistance level at which current either no longer flows or is reduced to an amount at which the heating element no longer increases in temperature, the threshold temperature of the PTC material of Example 2 is approximately 49° C. whereas the threshold temperature of the PTC material of Example 1 is approximately 57° C.

Figure 3B:
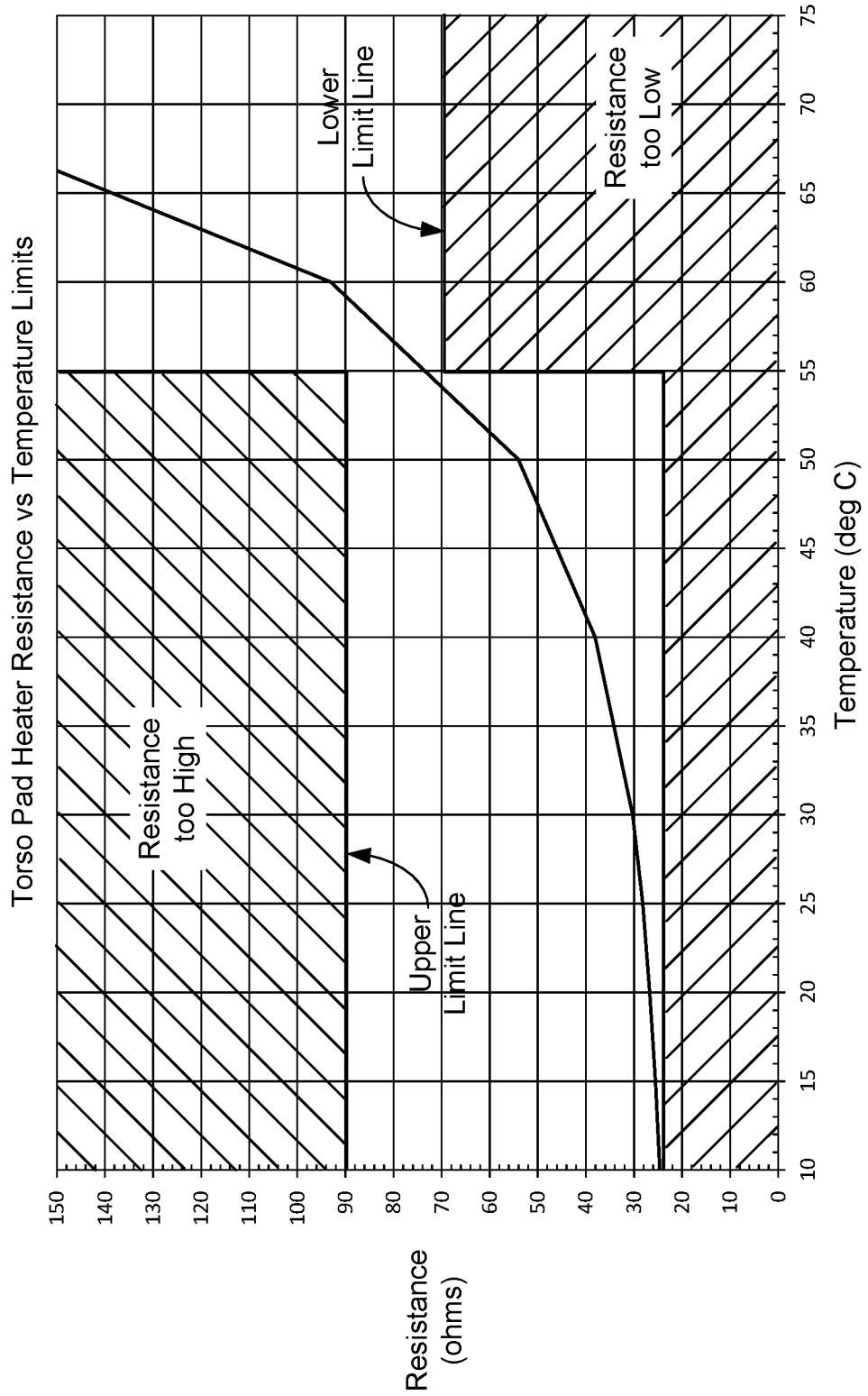

The PTC material may be selected and/or produced such that the resistance curve thereof falls within one or both of a lower limit and upper limit over a range of temperatures. The lower limit and/or upper limit may also vary over the range of temperatures. FIG. 3B shows a resistance curve of an exemplary heating element having the configuration of that shown in FIGS. 1 and 2. The tunability of the resistance curve of the PTC material may allow for the heating element to conform to the operating parameters and/or requirements of the patient warming system. For example, over an operating range of temperatures, the resistance curve of the PTC material may be higher than a lower limit at or below which too much current would be drawn by the heating element. Also, over an operating range of temperatures, the resistance curve of the PTC material may be lower than a upper limit at or above which the resistance is too high and impedes the flow of current.

Figure 3C:
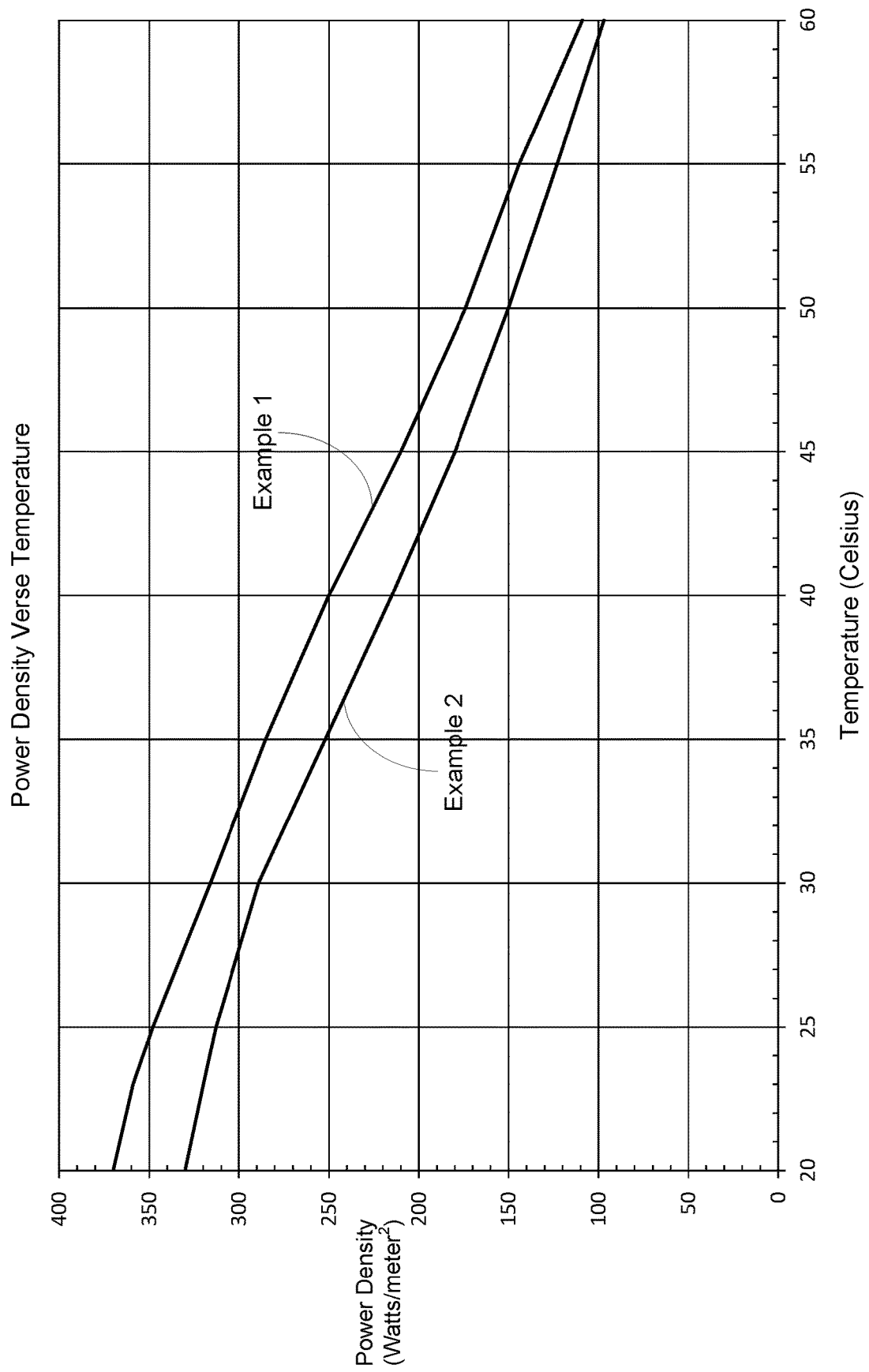
FIG. 3C shows an exemplary curve of exemplary heating elements having the configuration of that shown in FIGS. 1 and 2.

FIG. 3C shows the power density (watts per meter$^2$) relative to temperature. As shown, the power density of the PTC material decreases as temperature increases. Variation of factors such as the amount and/or type of electrical conductive material provided in the PTC material, and the amount and/or type of carrier material used in the PTC material can also affect the power density. In the example shown, Example 1 includes a PTC material having more electrical conductive material therein as compared with the PTC material of Example 2. At a given temperature, the power density (watts per meter$^2$) of the PTC material of Example 1 is higher than the resistance of the PTC material of Example 2.

In operation, the self-regulating characteristic for the heating element 30 is provided by way of a PTC effect that occurs when the heating element 30 is heated. The PTC material of the resistive layer 38 is configured to generate heat when voltage is applied across the busses 40, 42 via terminals 52, 68 that are provided for each bus 40, 42. In some embodiments, the PTC material may include a network in which one or more electrically conductive materials (e.g., carbon or one or more suitable conductive material) are dispersed in a polymer or other suitable carrier material. As the PTC material is heated, thermal expansion causes the PTC material to expand such that respective distances between conductive materials in the network increase, thereby increasing electrical resistance of the material at higher temperatures. The resistance curve of such PTC materials may be parabolic in shape, similar to that shown in FIGS. 3A and 3B. In other embodiments, as the PTC material is heated, the temperature of the PTC material rises until it exceeds a phase transformation temperature and the resistance of the heating element 30 rapidly increases. In such embodiments, the resistance curve of the PTC material may be more hyperbolic in shape as compared to the curves shown in FIGS. 3A and 3B.

When the threshold temperature is reached, the heating element 30 may be configured to throttle heat output when the threshold temperature of the PTC material is reached (due to the high resistance state), and will do so as long as the PTC material is at the threshold temperature. When the temperature of the PTC material is lowered, the resistance of the PTC material will decrease (e.g., due to the PTC material contracting and/or undergoing a reverse phase transformation). The PTC material therefore provides the heating element with a "self-regulating" temperature effect to help limit the heater from reaching temperatures above a predetermined value. The self-regulating temperature effect also helps to improve the thermal uniformity of the heating element.

The lamination 32 may in some embodiments include one or more additional layers. With reference to FIG. 2, the lamination 32 may include an additional insulating layer 58 adjacent the resistive layer 38. A fabric layer 60 may also be provided adjacent the additional insulating layer 58 such that the additional insulating layer 58 is disposed between the fabric layer 60 and resistive layer 38. The additional insulating layer 58 may in some embodiments be bonded to the resistive layer 38 using an adhesive, such as a pressure sensitive adhesive. The fabric layer 60 may be bonded to the additional insulating layer 58 using an adhesive, such as a pressure sensitive adhesive. The additional insulating layer 58 may be formed of any suitable insulating material, including polyethylene, PET, thermoplastic PU, or polyamide. The thicknesses of the additional insulating layer 58 may be between 10 and 50 micrometers. In some embodiments, the fabric layer 60 is made of a woven fabric material. In other embodiments, the fabric layer 60 is made of a nonwoven fabric material. The fabric layer may improve the durability of the lamination 32. It will be understood that while FIG. 2 shows an exemplary embodiment including the additional insulating layer 58 and the fabric layer 60 included in the lamination 32, in other embodiments one or both of these layers is omitted from the lamination 32.

Figure 4:
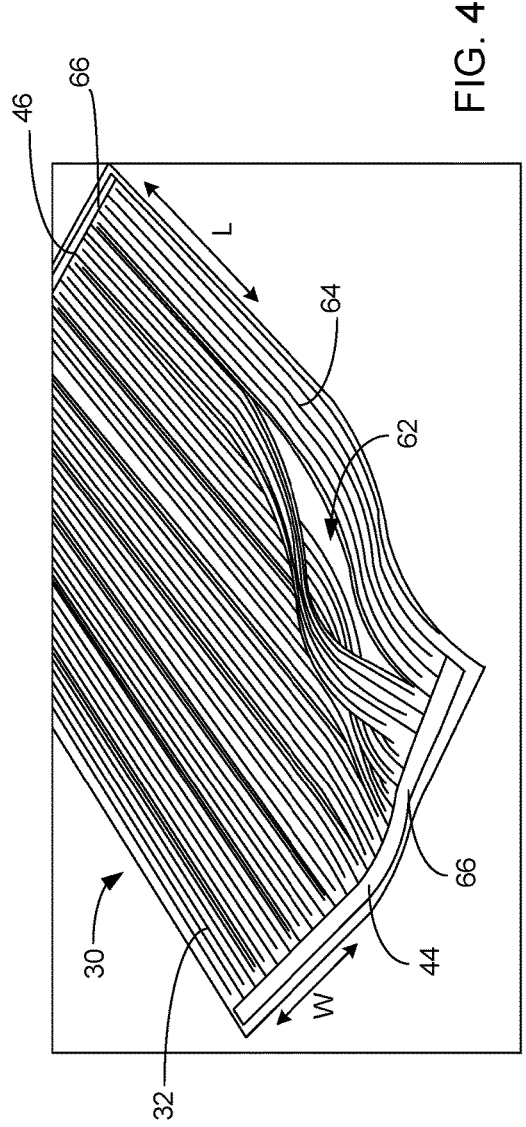
FIG. 4 is a top perspective view of the heating element of FIG. 1 showing a slit formed in the lamination.
Figure 5:
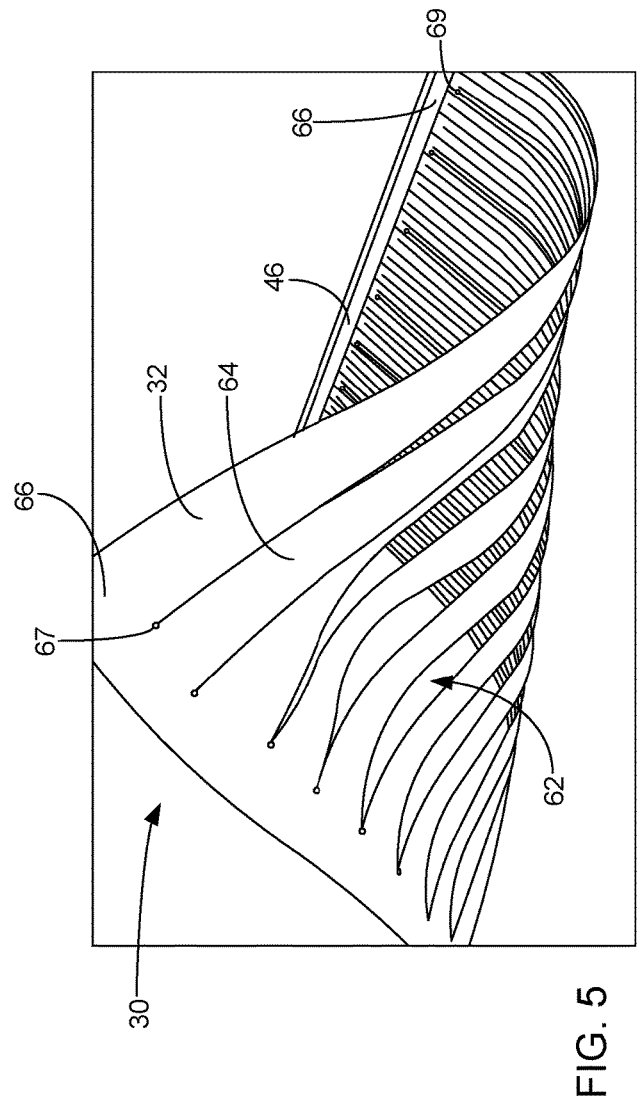
FIG. 5 is a bottom perspective view of the heating element of FIG. 1 showing the slits formed in the lamination.

Referring now to FIGS. 4 and 5, in some embodiments the lamination 32 includes a plurality of elongated slits 62. The slits may provide enhanced flexibility for the heating element 30 in addition to the flexible characteristics of the materials used in the lamination 32. For example, the slits 62 may improve the ability of the heating element 30 to be draped over a surface or a patient. In other embodiments, the slits 62 may improve pressure management of a pad including the heating element 30 when a patient lays on the pad. The flexibility is particularly advantageous in minimizing the risk of pressure ulcers that are formed from high patient contact pressure areas. The slits 62 may extend along the length L of the lamination 32. The slits 62 may be evenly spaced along the width W (as shown in FIG. 1) such that the slits 62 have an ordered arrangement along the lamination 32. In alternative embodiments, the slits may have different spacings in an ordered or unordered arrangement. The slits 62 may extend along most of the entire length L. The lamination 32 is segmented into parallel strips 64 by the slits 62 and each parallel strip 64 may have the same width and length. In alternative embodiments, the slits may have different lengths such that the strips 64 have different lengths and/or the slits may have different spacings such that the strips 64 have different widths. In some embodiments, each strip 64 has a width along the width direction W in a range of 1 cm to 20 cm. In other embodiments, each strip has a width along the width direction W in a range of 1 cm to 10 cm. The arrangement of the slits 62 and the strips 64 is exemplary and other configurations may be suitable to provide the desired flexibility of the heating element 30.

Any suitable number of slits 62 and strips 64 may be provided, and the number may be dependent on the size of the lamination 32 for a particular application. For example, between 5 and 20 slits and 5 and 20 strips may be present in a given lamination.

The strips 64 may extend along the length L of the lamination between the bus bases 44, 46, and respective fingers of the buses may extend along the strips 64 such that the arrangement of the slits 62 does not disrupt the electrical buses. The terminal ends 67, 69 of a given slit 62 are provided at a given distance away from the edges of the lamination in the length L direction. The portion of the lamination between the terminal end of the slit 62 and the edge of the lamination along the length L may be considered a supporting strip 66 to which the ends of each strip 64 may be attached. A supporting strip 66 of the lamination 32 may include a respective one of the bus bases 44, 46. In the embodiment shown, a supporting strip 66 is arranged on each side of the lamination 32.

Figure 6:
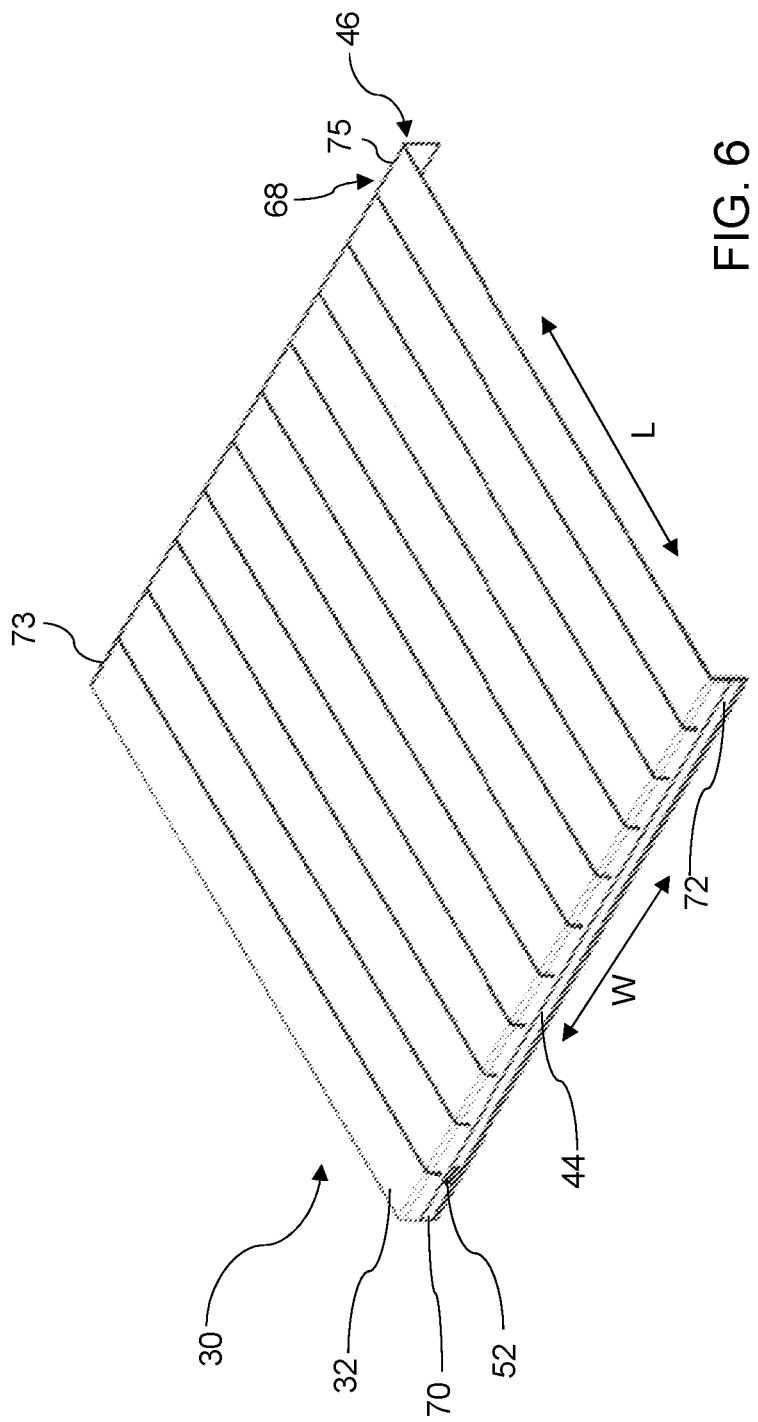
FIG. 6 is a perspective view of the heating element of FIG. 1 in an as-built condition and including diagonally opposed terminals that supply voltage to the heating element.

Referring now to FIG. 6 and FIG. 7A and FIG. 1, the terminals 52, 68 for the buses 40, 42 of the heating element 30 may be arranged to provide a counter current flow pattern across the conductive layers of the lamination 32. FIG. 6 shows the heating element 30 of FIG. 1 in an exemplary position corresponding to an exemplary installed state in which the edges of the lamination 32 are folded. The terminals 52 and 68 are arranged to be diagonally opposed relative to each other. The terminal 52 may be connected to a first end 70 of the first bus base 44 that is opposite a second end 72 in the width direction W. The terminal 68 may be connected to a second end 75 of the second bus base 46 that is opposite a first end 73 in the width direction W, such that the terminals 52, 68 are diagonally arranged on the lamination 32. The terminals 52, 68 may be connected to the bus bases 44, 46 via a riveting process, crimping process, or any other suitable process.

FIG. 7A shows the diagonal arrangement of the respective terminals 52, 68, which provides the counter current flow pattern across the conductive layers of the lamination 32. The counter current flow pattern may help to further improve the uniformity in voltage being applied across the conductive layers of the lamination 32. FIG. 7A shows an exemplary test setup applied to a heating element shown in FIG. 6 in which the terminals 52, 68 are connected in the diagonal arrangement, and crimps are placed at locations 77A-77F to measure voltage across the conductive layers of the lamination 32 at different points. The test setup applies 47 V, and the respective recorded voltages are shown in the figure. In FIG. 7A, flow lines parallel to the length direction L are all within 0.2 V of one another. This is contrasted with the test setup shown in FIGS. 7B and 7C, where the terminals are connected in different, non-diagonal arrangements. As shown, the variation in voltage flow lines parallel to the length direction L are greater than that shown in FIG. 7A.

The counter current flow may therefore help in providing an improved uniformity in the application of power. This, in combination with the PTC material of the resistive layer, may provide the heating element 30 with an improved uniformity in distribution of heat and a specific watt density as a function of temperature.

One or more instances of the heating element 30 may be included in a warming device. The warming device may be any suitable device for providing electrically conductive warming, such as an underbody pad (e.g., torso pad), overbody blanket, under-body blanket, headrest, and the like. In some embodiments, the warming device may be used for warming a patient, and may be used in a patient warming system as the only warming device or in combination with one or more other warming devices. In addition to one or more heating elements 30, the warming device may include one or more foam layers, one or more spacer layers, one or more temperature sensors, and a cover. The number, specific arrangement, and respective thicknesses of the layers of a given warming device may depend on its particular application. Exemplary warming device constructions are described below.

With reference to FIGS. 8-10, an exemplary warming device is shown embodied as an underbody pad 100 (e.g., torso pad). In the embodiment shown, the underbody pad 100 is sized and shaped to support a torso of a patient and may have any suitable shape. The underbody pad 100 may have a head side 101a to be placed proximate the head of a patient, and a perineal cutout 101b opposite the head side. The layers of the underbody pad 100 are vertically stacked in a thickness direction, orthogonal to the length and width dimensions of the underbody pad.

The underbody pad 100 includes a base foam layer arrangement 80 adjacent the heating element 30. The base foam layer arrangement 80 may be adjacent a bottom layer of the heating element 30. In some embodiments, the base foam layer arrangement is a single foam layer. In other embodiments such as that shown in FIGS. 8 and 9, the base foam layer arrangement includes two or more stacked layers of different foams. The foams in the base foam layer arrangement 80 may include at least one of a high-density foam, a medium density foam, and a base viscoelastic foam. The arrangement and thicknesses of the different foams of the foam layer arrangement 80 may be dependent on the application. In the embodiment shown, a high density foam layer 106 forms the bottom layer, a medium density foam layer 108 is arranged adjacent the high density foam layer 106, and a viscoelastic foam layer 110 formed of a viscoelastic material is arranged adjacent the medium density foam layer 108 opposite the high density foam layer 106. The layers in the base foam layer arrangement 80 may be bonded with any suitable adhesive material. The viscoelastic foam layer 110 may improve the ability of the heating element 30 to move for pressure management of the patient by spreading out the patient loading with a minimum increase in pressure. The medium-density foam layer 108 and the high-density foam layer 106 may help in building volume in the underbody pad 100 and may provide insulation for directing heat towards the patient. The foam layers 106, 108 also may be used for pressure management.

Any suitable materials and thicknesses for the foam layers may be selected. In some embodiments, each layer in the base foam layer arrangement 80 may have a thickness that is between 0.5 cm and 5 cm. Accordingly, in some embodiments, the base foam layer arrangement 80 may have a thickness of 1.5 cm and 15 cm. In one example, the high density foam layer 106 has a thickness that is around 3.2 centimeters, the medium-density foam layer 108 has a thickness that is around 1.27 centimeters, and the viscoelastic foam layer 110 may have a thickness that is around 1.27 centimeters.

The high density foam layer 106 may have a density that is between 43.2 and 46.5 kilograms per cubic meter, and an indentation force deflection that is between 3.7 and 4.6 kilograms per square centimeter. The medium density foam layer 108 may have a density that is between 28 and 31 kilograms per cubic meter, and an indentation force deflection that is between 3.1 and 3.9 kilograms per square centimeter. The viscoelastic foam layer 110 may have a density that is around 1.8 kilograms, and an indentation force deflection that is around 2.1 kilograms per square centimeter.

The heating element 30 may have a thickness (extending in a direction between the major surfaces 33, 35) that is between 1.2 and 1.8 millimeters. In one example, the heating element 30 has a thickness that is around 1.5 millimeters. As shown in FIGS. 6, 8 and 9, the heating element 30 may wrap down around the edges of the base foam layer arrangement 80 such that the bus bars of the heating element 30 are located on sides of the underbody pad 100. This wrapping of the heating element along the edges of the base foam layer arrangement 80 may increase or maximize the heated area of the underbody pad 100. Additionally, wrapping the heating element 30 along the edges of the base foam layer arrangement 80 may reduce the non-radiolucent areas on the underbody pad 100 and protects the bus bases, terminals, and wiring from pressure applied to the underbody pad by a patient in contact therewith. Furthermore, wrapping the heating element 30 along the edges of the base foam layer arrangement may increase or maximize the area of the major surface of the underbody pad that is covered by the slit and strip portion of the heating element 30, which may improve flexibility and pressure management of the warming device. Moreover, wrapping the heating element 30 along the edges of the base foam layer arrangement 80 may help to improve comfort of a user by keeping components of the heating element 30 such as the bus bases, terminals, and wiring off of the major surface on which the patient is placed.

It will be appreciated that while the exemplary embodiment shows a single heating element, in other embodiments the warming device (e.g., underbody pad) may include more than one heating element. These heating elements may be adjacently arranged and collectively form a heating element layer 30.

The layers disposed above the heating element 30 include the spacer layer 82, foam layer 104, and additional spacer layer 84. These upper layers may be configured to provide a minimal temperature drop across the layers to enable a lower operating temperature of the heating element 30. In some embodiments, in operation with a patient placed on the underbody pad, the temperature at the uppermost surface of the warming device (surface temperature) is within 5° C. of the temperature of the heating element. In other embodiments, in operation with a patient placed on the underbody pad, the temperature at the uppermost surface of the warming device (surface temperature) is within 4° C. of the temperature of the heating element. In other embodiments, in operation with a patient placed on the underbody pad, the temperature at the uppermost surface of the warming device (surface temperature) is within 3° C. of the temperature of the heating element. The lower operating temperature may improve the durability of a mattress that is arranged below the underbody pad 100 since the mattress foam will have less of a tendency to break down as compared with a situation where the mattress is subject to higher temperatures in order to compensate for a higher temperature drop across the layers. The upper layers also enable the heating element 30 to have a smaller transition from being turned off or cold to the operating temperature such that the warmup time for the heating element 30 is faster.

The spacer layer 82 is arranged adjacent the heating element 30 opposite the base foam layer arrangement 80. The spacer layer 82 may include any suitable material, such as a woven or nonwoven fabric material that is configured for thermal conduction, natural convection and radiation modes of heat transfer. In some embodiments, the spacer layer 82 is formed of a polyester or other suitable material. The spacer layer material may have a density that is between 48 and 65 kilograms per cubic meter. The spacer layer material may have a mass per unit area that is between 550 and 570 grams per square meter. The spacer layer 82 may have a thickness that is between 5 and 20 millimeters. In an example, the spacer layer 82 has a thickness of around 10 millimeters. The thickness of the spacer layer 82 may in some embodiments be greater than a thickness of the heating element 30.

The foam layer 104 is arranged adjacent the spacer layer 82 opposite the heating element 30. The foam layer 104 may be a viscoelastic material. In some embodiments, the foam layer 104 is made of a polyurethane foam. The foam layer 104 and the spacer layer 82 may form a subassembly that is arranged adjacent the heater element 30 opposite the base foam layer arrangement 80. The foam layer 104 and the spacer layer 82 may be bonded together using any suitable method or material (e.g., adhesive, sonic welding, etc.). The foam layer 104 may have a thickness that is between 1 and 15 millimeters. In an example, the foam layer 104 has a thickness of around 3.5 millimeters.

The foam layer 104 may smooth out bony prominences in the underbody pad 100. The spacer layer 82 may assist in providing bulk pressure management in that the material has reliefs which enable the fabric to move freely. Furthermore, using the spacer fabric material together with the foam layer may be advantageous as compared with using only a foam material, in that the spacer fabric is formed of a material having less density and a lower thermal resistance as compared with the foam layer (e.g., which may be made of polyurethane foam), such that the spacer fabric material may enable a faster warming time for the warming device. For example, the thermal conductivity of the spacer fabric material may be between 0.160 and 0.170 watts per meter per degree Celsius, which is higher than that of polyurethane foam.

In an exemplary embodiment, the spacer layer 82 may have a thickness that is around 10 millimeters and the foam layer 104 may have a thickness that is around 3.5 millimeters. The foam layer 104 may be formed of the same material as the viscoelastic foam layer 110. The thicknesses of the layers are merely exemplary, and many different thicknesses may be suitable.

The additional spacer layer 84 is arranged adjacent the foam layer 104 opposite the spacer layer 82. The additional spacer layer 84 may be formed of the same type of material as the spacer layer 82 (e.g., polyester or another suitable material), although the specific structure and/or thickness may be different as compared with the spacer layer 82. In some embodiments the additional spacer layer 84 is a woven fabric material. The additional spacer layer 84 may be a flexible material that provides point elasticity and also covers wiring and the temperature sensor assembly 102 that may be disposed between the spacer layer 84 and the foam layer 104. Thus, the additional spacer layer 84 may be used to enhance the feeling of the underbody pad 100 against a patient. In other embodiments, the additional spacer layer 84 may be a nonwoven fabric material. The additional spacer layer may have a thickness that is between 2 millimeters and 8 millimeters. In an example, the additional spacer layer 84 may have a thickness that is around six millimeters. The additional spacer layer 84 may have a thickness that is less than a thickness of the spacer layer 82.

As shown in FIGS. 8 and 9, the additional spacer layer 84 may wrap down around the edges of at least a portion of the other layers of the layer stack (e.g., foam layer 104, spacer layer 82, heating element 30, and/or one or more layers of the base foam layer arrangement 80) such that portions of the additional spacer layer 84 extend along the thickness direction proximate the sides of the underbody pad 100.

A temperature sensor assembly 102 includes one or more temperature sensors 105. Each of the temperature sensors 105 may include one or more thermistors 88 and a heat spreader 116 (FIGS. 12A-12C). Although in other embodiments, the temperature sensors 105 may not include a heat spreader. The temperature sensor assembly 102 may be arranged between the foam layer 104 and the additional spacer layer 84. The location of the temperature assembly between the foam layer 104 and the additional spacer layer 84 provides the temperature assembly near the upper surface of the underbody pad 100, but also provides pressure management by including the additional spacer layer as an intervening layer between the temperature sensor assembly and the upper most layer (e.g., cover) of the warming device, which may help to reduce or minimize the feeling of a protuberance due to the presence of a temperature sensor.

A wiring assembly 103 may connect the warming device to a control unit (exemplified in FIG. 21), and in this connected state the heating element 30 may be coupled to a voltage supply via the control unit. The temperature sensor assembly 102 may be coupled to the control unit via this connection for use in controlling application of power to the heating element. The wiring assembly 103 may include ribbon cables 118 routed in the warming device and respectively coupled to the temperature sensor assembly 102 and the heating element 30. The use of ribbon cable 118 may reduce x-ray artifacts. The ribbon cables 118 may be routed in straight lines rather than curved lines so that any x-ray artifacts left by the ribbon cables can be easily distinguished from human anatomy for a surgical patient. In some embodiments, the ribbon cable 118 may be bonded to the PTC heating element 30 and a part of the ribbon cable 118 may pass through the spacer layer 82 and foam layer 104 to couple to one or more temperature sensors 105 the temperature sensor assembly 102. The wiring assembly 103 may also include a printed circuit board assembly (PCBA) 121 that may provide an interface between the ribbon cable 118 and wiring for coupling the warming device to the control unit. The PCBA 121 may be potted for protection and may in some embodiments also include one or more resistors for use by the control unit in identification of the warming device and the setting of a temperature cutoff threshold. The wiring assembly 103 may also include one or more cables 123 coupled at one end thereof to the PCBA 121 and coupled at the other end thereof to a plug 120 (connector) for coupling to a control unit.

A cover 78 encloses the layers of the warming device. The cover 78 may be formed of one sheet that wraps around the top and the bottom of the underbody pad 100 and is welded on three sides. In other embodiments, other configurations of the cover 78 including more than one sheet may be suitable. The cover 78 is formed to prevent liquid ingress in the underbody pad 100 and may in some embodiments be formed of a four-way stretchable material. The four-way stretchable material may have a stretchability that is between 75% and 200%. In some embodiments, the cover material is a knit nylon material coated with a thermoplastic polyurethane. The cover 78 may be an interfacing layer with a patient such that the cover 78 directly contacts the skin. A hypoallergenic material may be used in the cover 78 to prevent skin reaction.

With reference to FIGS. 10 and 11, the temperature sensors 105 of the temperature sensor assembly 106 are arranged in a pattern 114. The pattern may help to ensure patient contact with at least one of the sensors to accommodate a variety of patient body types and positions. The pattern may be an ordered distribution or an unordered distribution of the temperature sensors 105. The temperature sensors 105 may be evenly spaced or have a varying space therebetween. As shown in FIG. 10, an exemplary pattern include six temperature sensors 105 that are arranged in a staggered arrangement. As shown in FIG. 11, the pattern 114 may help to ensure that even a small patient having a length LP as small as 79 centimeters will cover at least one of the temperature sensors 105 in the pattern 114.

As described above, in some embodiments, each of the temperature sensors 105 may include one or more thermistors 88 and a heat spreader 116. Referring in addition to FIGS. 12A-12C, exemplary temperature sensors 105 are shown including a thermistor 88 bonded to a heat spreader 116. The thermistor 88 may be bonded to the heat spreader 116 by a thin acrylic bond. The heat spreader 116 may be made of a pyrolytic graphite sheet. In an exemplary embodiment, the graphite sheet may have a thermal conductivity in an x-y plane that is around 1,900 watts per meter-Kelvin and a thermal conductivity in a z plane that is around 15 watts per meter-Kelvin. In other embodiments, other materials having similar thermal conductivity properties may be suitable for the heat spreader 116 as an alternative to the pyrolytic graphite sheet. In some embodiments (and with continued reference to FIGS. 8 and 9), the heat spreader 116 may be bonded to the foam layer 104 via an adhesive.

In the example shown in FIG. 12A, the heat spreader 116 has a clover leaf type shape that includes four arms 117A, 117B, 117C, 117D radially extending from a central portion 119. Each arm increases in width along at least a portion of its length as it extends from the central portion. Spaces are provided between adjacent arms. The length of a given arm in the radial direction may be greater than the length (e.g., diameter) of the central portion. This shape may provide an increased surface area while also maintaining flexibility. This flexibility may help in improving pressure management when the heat spreader is included in the warming device. In other embodiments, the heat spreader 116 may be formed to have other geometric shapes. FIGS. 12B and 12C show other exemplary heat spreader shapes. In FIG. 12B, the heat spreader has a circular shape. In FIG. 12C, the heat spreader has a flower shape that includes 8 arms extends from a central portion. In other embodiments, the heat spreader may have a different suitable shape (e.g., square, rectangle, hexagon, octagon, other polygonal shape, other flower shape having a different number of arms, etc.).

One consideration in connection with the use of a heat spreader may be pressure management. Depending on the location of the heat spreader in a warming device such as a warming pad, the presence of a heat spreader may cause a pressure point and/or may be felt by a patient. If the heat spreader creates a pressure spot, a patient may be subjected to pressure for long periods of time and there may be a risk of developing pressure ulcers. Therefore, the heat spreaders should be minimally perceivable when handling and using the warming device.

Table 1 provides the results of heat spreader pressure management testing that was conducted using the heat spreader shapes shown in FIGS. 12A-12C as compared with the absence of a heat spreader (control). The heat spreaders were each included in an underbody pad as shown in FIGS. 8 and 9. A 0.5 kg weight was placed on the heat spreader for 7 minutes (to reach steady-state), and pressure was measured. For the control, a 0.5 kg weight was placed on the underbody pad in an area with no heat spreader for 7 minutes (to reach steady-state), and pressure was measured. Both the average and maximum pressure measurements were recorded over the area. The average pressure measurement provides the average of the point measurements for a given test area. While the average measurement is useful, it is maximum pressure that will cause discomfort and pressure ulcers. Use of the heat spreader shown in FIG. 12A had the least increase in maximum pressure as compared with the control.

TABLE 1

Heat Spreader Pressure Management Testing

| Test | Average Pressure mmHg | Maximum Pressure (mmHg |
|---|---|---|
| Control (no heat spreader) | 23.22 | 59.52 |
| FIG. 12A heat spreader | 27.16 (+17%) | 68.55 (+15%) |
| FIG. 12B heat spreader | 26.52 (+14%) | 79.5 (+34%) |
| FIG. 12C heat spreader | 29.83 (+28%) | 84.57 (+42%) |

It will be appreciated that while in some embodiments a heat spreader may be used, in other embodiments heat spreaders may be omitted from the temperature sensor assembly 102.

Control of the warming device (e.g., underbody pad) may be conducted using one or more temperature sensors of the warming device. One or more temperature sensors of the warming device may be used in the control of a heating zone of the warming device. In some embodiments, one heating element is associated with a given heating zone and the one or more temperature sensors associated with that given heating zone may be used in the control of that heating element. In other embodiments, more than one (e.g., 2, 3, 4, etc.) heating element is associated with a given heating zone and the one or more temperature sensors associated with that given heating zone (and with the respective heating elements therein) may be used in the control of all of the heating elements in that given zone. In some embodiments, a warming device may have a single heating zone. In other embodiments, a warming device may have more than one heating zone. In some implementations of the more than one heating zone embodiments of the warming device, the heating zones may each have the same number of heating elements. In some implementations of the more than one heating zone embodiments of the warming device, the heating zones may have different respective numbers of heating elements. It will be appreciated that reference to a temperature sensor being associated with a heating element also may constitute reference to the temperature sensor being associated with a heating zone. It will also be appreciated that the number of temperature sensors for a given warming device, and the number of temperature sensors associated with a given heating element, is not limited to the particular number depicted in the example.

Figure 13:
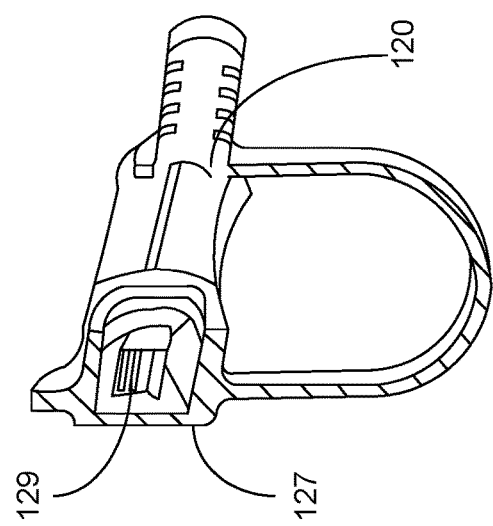
FIG. 13 is a perspective sectional view of an exemplary plug that may be coupled to a warming device.

As described above, the wiring assembly 103 may include one or more cables 123 coupled at one end thereof to the PCBA 121 and coupled at the other end thereof to a plug 120 (connector) for coupling to a control unit. FIG. 13 shows further details of the plug 120 that may be coupled to a control unit. The plug 120 includes an interface 129 and a removable cap 127 for covering the interface 129. The one or more cables 123 may be coupled to the interface 129 of the plug. With additional reference to FIG. 14, the one or more cables may be bundled together as a single cord 125. A cord grommet 124 is adhered to the cover 78 and the cord passes through the cord grommet. Any suitable adhesive may be used to adhere the face of the grommet 124 to the cover 78. The cord grommet 124 is configured to prevent the cord 103 from pulling out of or tearing the cover 78.

Figure 15:
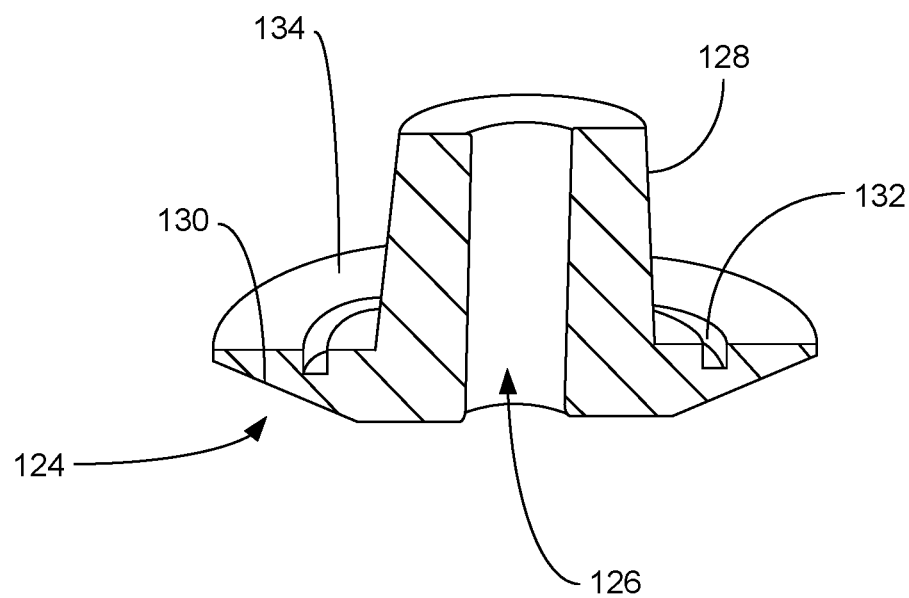
FIG. 15 is a side sectional view of the grommet of FIG. 14.

FIG. 15 shows the grommet 124 having a bore 126 that is formed to have an interference fit with the cable 125 inserted through the grommet 124 to provide mechanical retention and sealing. In an exemplary embodiment, the interference may be between 0.2 and 0.8 millimeters. The grommet 124 may also have a tapered peripheral surface 128 that tapers radially inwardly from a face 130 of the grommet 124 into a corresponding receiving aperture in the underbody pad 100. The tapered peripheral surface 128 enables centering of the grommet 124 on a hole of the receiving aperture. An adhesive glue pocket 132 may also be formed in a wall 134 of the grommet 124 that defines the face 130. The adhesive glue pocket 132 may be formed as a circumferential groove in the wall 134. In some embodiments, an ethyl or butyl cyanoacrylate adhesive liquid may be used to provide bonding and water-tight sealing.

Referring now to FIG. 16, a method 138 of manufacturing the underbody pad 100 (as shown in FIGS. 8 and 9) is shown. Step 140 of the method 138 includes forming the base foam layer arrangement 80. Step 140 may include bonding two or more foam layers that are used to form the base foam layer arrangement 80. Step 140 may also include cutting a profile of the base foam layer arrangement 80 from the one or more foam materials that make up the base foam layer arrangement 80.

Step 142 of the method 138 includes arranging the heating element 30 and the temperature sensor assembly 102 on the base foam layer arrangement 80. Step 142 may include applying heat and pressure to cure an adhesive between the heating element 30 and the base foam layer arrangement 80. Step 142 may also include connecting the heating element 30 to the wiring assembly 103.

Step 144 of the method 138 includes bonding the foam layer 104 to the spacer layer 82. Step 144 may include ultrasonic welding, application of adhesive, or any other suitable securing method. The bonding may be conducted by perimeter bonding the layers. As such, the layers may not be bonded inside the perimeter, which may assist with pressure management and/or flexibility/conformability of the warming device. The size of the perimeter bond may be any suitable size. In one example, the perimeter bond is a 51 mm (two inch) perimeter bond. Step 144 may also include cutting the profile for the bonded the top viscoelastic foam layer 104 and spacer layers 82, 84.

Step 146 of the method 138 includes arranging the top foam assembly including the foam layer 104 bonded to the spacer layer 82 on top of the base foam layer arrangement 80 including heating element 30 and the base foam layer arrangement 80, while inserting the temperature wiring of the wiring assembly 103 through the top assembly. Step 146 may include applying adhesive on top of the heating element and/or to the spacer layer. Step 146 may also include curing the adhesive. In some embodiments, the bonding may be a perimeter bond (e.g., a 51 mm perimeter bond) and the adhesive is applied only at the perimeter of the heating element and/or spacer layer 82.

Step 148 of the method 138 includes laying the heat spreaders 116 on top of the thermistors. Heat and pressure may be applied to cure the adhesive for attaching the heat spreaders 116 to the viscoelastic foam layer 104. It will be appreciated that in embodiments in which the heat spreaders are not included, this step may be omitted.

Step 150 of the method 138 includes bonding the additional spacer layer 84 to the foam layer 104. Step 150 may include ultrasonic welding, application of adhesive, or any other suitable securing method. The bonding may be conducted by perimeter bonding the layers. The size of the perimeter bond may be any suitable size. In one example, the perimeter bond is a 51 mm perimeter bond. The edges of the additional spacer layer 84 may be wrapped on the sides of the stack and may in some embodiments be bonded thereto.

Step 152 of the method 138 includes inserting the layered structure into the cover 78 and ultrasonically welding, sewing, or gluing edges of the cover 78 to enclose the structure and prevent liquid ingress. Step 152 may also include feeding the cord of the wiring assembly 103 through the cover and sealing the cable on the outside of the cover using the grommet (e.g., using glue).

Referring now to FIGS. 17 and 18, an exemplary warming device is shown embodied as an over-body blanket 200. The layers of the over-body blanket 200 are vertically stacked in a thickness direction T, orthogonal to the length L and width W dimensions of the over-body blanket. The layers of the blanket 200 include foam layer 110, heating element 30, spacer layer 82, temperature sensor assembly 102, wiring assembly 103, and cover 78.

It will be appreciated that while the exemplary embodiment shows a single heating element, in other embodiments the warming device (e.g., over-body blanket) may include more than one heating element. These heating elements may be adjacently arranged and collectively form a heating element layer 30.

The over-body blanket 200 includes a foam layer 110 adjacent the heating element 30. The foam layer 110 may be a viscoelastic material. In some embodiments, the foam layer 110 is made of a polyurethane foam. The foam layer 110 may be formed of the same material as the viscoelastic foam layer 110 described above in connection with the exemplary underbody pad 100. In some embodiments, the foam layer 110 may have a thickness that is between 0.5 centimeters and 2 centimeters. In an example, the foam layer 110 may have a thickness of 6.35 millimeters. The foam layer 110 may have a density that is around 1.8 kilograms, and an indentation force deflection that is around 2.1 kilograms per square centimeter. The foam layer 110 may be bonded to the heating element 30 at their outer perimeters The viscoelastic foam layer 110 provides an insulation layer for directing heat toward the patient and increasing a conformability of the blanket 200. Still a further advantage of the viscoelastic foam layer 104 is that the layer is a uniform, evenly distributed, weighing layer for the blanket 200, such that pressure may be spread out over the blanket 200, for example, when a clinical staff places weight on the blanket 200.

In contrast to the underbody pad 100, the heating element 30 may not be wrapped around the edges of the foam layer 110. The heating element 30 may have a thickness (extending in a direction between the major surfaces 33, 35) that is between 1.2 and 1.8 millimeters. In one example, the heating element 30 has a thickness that is around 1.5 millimeters.

The spacer layer 82 is arranged adjacent the heating element 30, opposite the foam layer 110. The spacer layer 82 may include any suitable material, such as a woven or nonwoven fabric material that is configured for thermal conduction, natural convection and radiation modes of heat transfer. In some embodiments, the spacer layer 82 is formed of a polyester or other suitable material. The spacer layer 82 may further include a fabric including latex to match the stretch of the viscoelastic foam layer 104 such that the materials may stretch together when bonded. The spacer layer material may have a density that is between 48 and 65 kilograms per cubic meter. The spacer layer material may have a mass per unit area that is between 550 and 570 grams per square meter. The spacer layer 82 may have a thickness that is between 5 and 20 millimeters. In an example, the spacer layer 82 has a thickness 6.10 millimeters. The thermal conductivity of the spacer fabric material may be between 0.160 and 0.170 watts per meter per degree Celsius.

The spacer layer 82 may provide a separation layer between the heating element 30 and the contact surface. An acrylic adhesive tape may be used to attach the heating element 30 and the spacer layer 82 at their outer perimeters.

Figure 19:
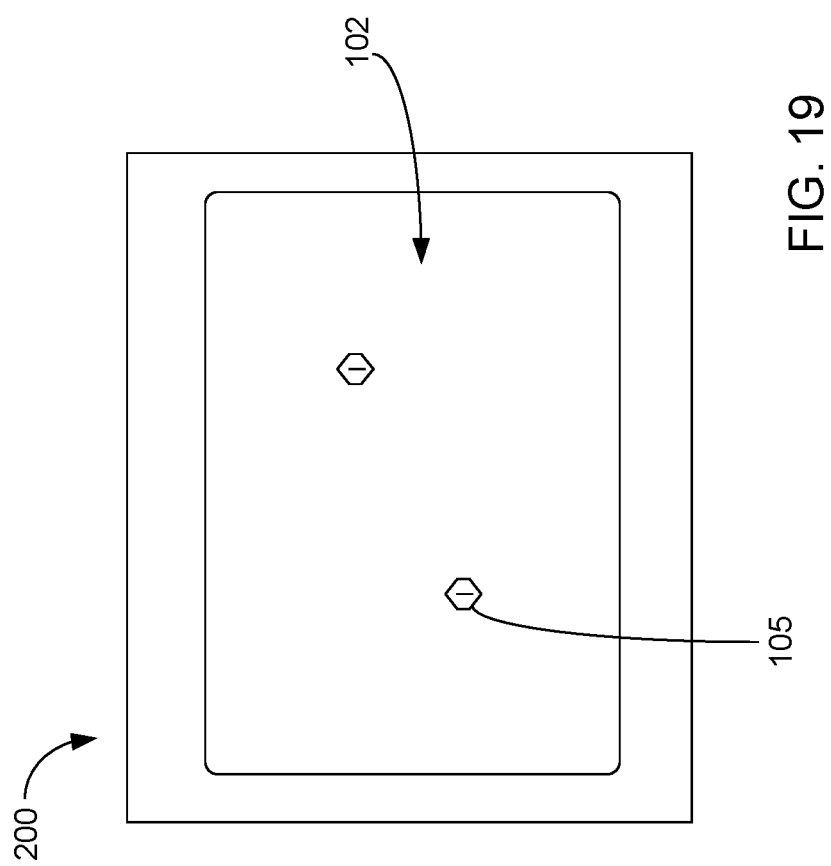
FIG. 19 is a top view of the exemplary blanket of FIG. 17.

A temperature sensor assembly 102 includes one or more temperature sensors 105. Each of the temperature sensors 105 may include one or more thermistors and a heat spreader (e.g., FIGS. 12A-12C). Although in other embodiments, the temperature sensors 105 may not include a heat spreader. The temperature sensor assembly 102 may be arranged between the spacer layer 82 and the cover 78. In the over-body blanket 200, the heat spreaders 116 (if included) may be attached to the spacer layer 82. The thermistors of the temperature sensor assembly 102 and the heat spreaders 116 (if included) may be attached to the spacer layer 82 via a spray adhesive. FIG. 19 shows an over-body blanket including an exemplary arrangement of temperature sensors 105. As shown, two temperature sensors are arranged in a staggered arrangement. In other embodiments, temperature sensors (e.g., two or more) may be arranged in a pattern having an ordered distribution or an unordered distribution of the temperature sensors. The temperature sensors 105 may be evenly spaced or have a varying space therebetween.

Control of the warming device (e.g., over-body blanket) may be conducted using one or more temperature sensors of the warming device. One or more temperature sensors of the warming device may be used in the control of a heating zone of the warming device. In some embodiments, one heating element is associated with a given heating zone and the one or more temperature sensors associated with that given heating zone may be used in the control of that heating element. In other embodiments, more than one (e.g., 2, 3, 4, etc.) heating element is associated with a given heating zone and the one or more temperature sensors associated with that given heating zone (and with the respective heating elements therein) may be used in the control of all of the heating elements in that given zone. In some embodiments, a warming device may have a single heating zone. In other embodiments, a warming device may have more than one heating zone. In some implementations of the more than one heating zone embodiments of the warming device, the heating zones may each have the same number of heating elements. In some implementations of the more than one heating zone embodiments of the warming device, the heating zones may have different respective numbers of heating elements. It will be appreciated that reference to a temperature sensor being associated with a heating element also may constitute reference to the temperature sensor being associated with a heating zone. It will also be appreciated that the number of temperature sensors for a given warming device, and the number of temperature sensors associated with a given heating element, is not limited to the particular number depicted in the example.

A wiring assembly 103 may connect the warming device to a control unit (exemplified in FIG. 22), and in this connected state the heating element 30 may be coupled to a voltage supply via the control unit and the temperature sensor assembly 102 may be coupled to the control unit for use in controlling application of power to the heating element. The wiring assembly 103 may include ribbon cables 118 routed in the warming device and respectively coupled to the temperature sensor assembly 102 and the heating element 30. The ribbon cables 118 may be routed in straight lines rather than curved lines so that any x-ray artifacts left by the ribbon cables can be easily distinguished from human anatomy for a surgical patient. In some embodiments, the ribbon cable 118 may be bonded to the heating element 30 and a part of the ribbon cable 118 may pass through the spacer layer 82 and foam layer 104 to couple to the temperature sensor assembly 102. The wiring assembly 103 may also include a printed circuit board assembly (PCBA) 121 that may provide an interface between the ribbon cable 118 and wiring for coupling the warming device to the control unit. The PCBA 121 may be potted for protection and may in some embodiments also include one or more resistors for use by the control unit in identification of the warming device and the setting of a temperature cutoff threshold. The wiring assembly 103 may also include one or more cables 123 coupled at one end thereof to the PCBA 121 and coupled at the other end thereof to a plug 120 for coupling to a control unit.

Figure 14:
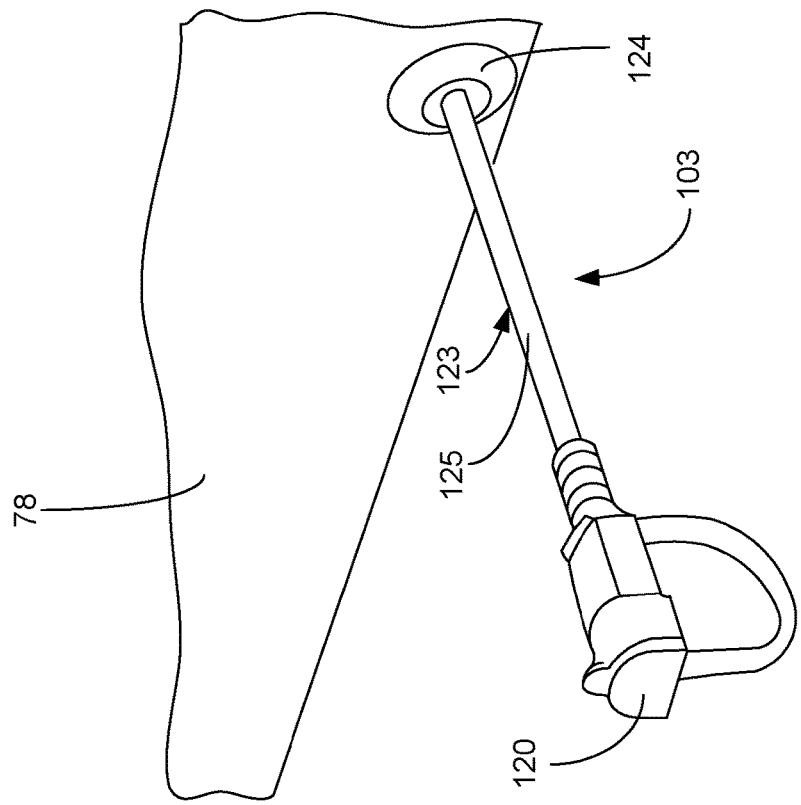
FIG. 14 is a perspective view of the plug of FIG. 13 coupled to a cable of a wiring assembly and showing the cord of the wiring assembly attached to a grommet secured to a cover of an exemplary warming device.

Any of the detailed features of the temperature sensor assembly 102 and the wiring assembly 103, as well as the detailed features of the plug 120, cord 125, and grommet 124 shown in FIGS. 13-15 as described above with respect to the underbody pad 100 may also be implemented in the blanket 200, and will not be repeated for the sake of brevity.

A cover 78 encloses the layers of the warming device. The cover 78 may be formed of one sheet that wraps around the top and the bottom of the over-body blanket 200 and is welded on three sides. In other embodiments, other configurations of the cover 78 including more than one sheet may be suitable. The cover 78 is formed to prevent liquid ingress in the over-body blanket 200 and may in some embodiments be formed of a four-way stretchable material. The four-way stretchable material may have a stretchability that is between 75% and 200%. In some embodiments, the cover material is a knit nylon material coated with a thermoplastic polyurethane. The cover 78 may be an interfacing layer with a patient such that the cover 78 directly contacts the skin. A hypoallergenic material may be used in the cover 78 to prevent skin reaction. The cover 78 also provides drapability due to the cover 78 being formed of a four-way stretchable material. The cover 78 may be ultrasonically welded to the structure of the blanket 200 and the fabric of the spacer layer 82 may be attached to the cover 78 via ultrasonically welded edges using a tape, such as a urethane tape. In other embodiments, the cover may be sewn or glued to the structure of the blanket.

In an exemplary embodiment of the blanket 200, the viscoelastic foam layer 104 may have a thickness that is around 6.35 millimeters, the heating element 30 may have a thickness that is around 1.52 millimeters, and the spacer layer 82 may have a thickness that is around 6.10 millimeters.

The spacer layer 82 may be bonded to the cover layer 78. The bonding of the spacer layer 82 and the cover layer 78 may be by adhesive, ultrasonic welding, sewing, or any other suitable securing method. In some embodiments, the bonding is conducted by perimeter bonding the spacer layer 82 to the cover layer 78. As such, the layers may not be bonded inside the perimeter. The size of the perimeter bond may be any suitable size. In one example, the perimeter bond is a 51 mm perimeter bond. In other embodiments, the bonding between the spacer layer 82 and the cover layer 78 is a full surface bond. The heating element 30 and the foam layer 110 may also be perimeter bonded (e.g., 51 mm perimeter bond) to each other, and the heating element may also be perimeter bonded (e.g., 51 mm perimeter bond) to the spacer layer 82. The perimeter bonding of the layers of the over-body blanket may provide for good drapeability (e.g., as a result of reduced sheer among the layers), and may prevent rucking of the layers.

Figure 20:
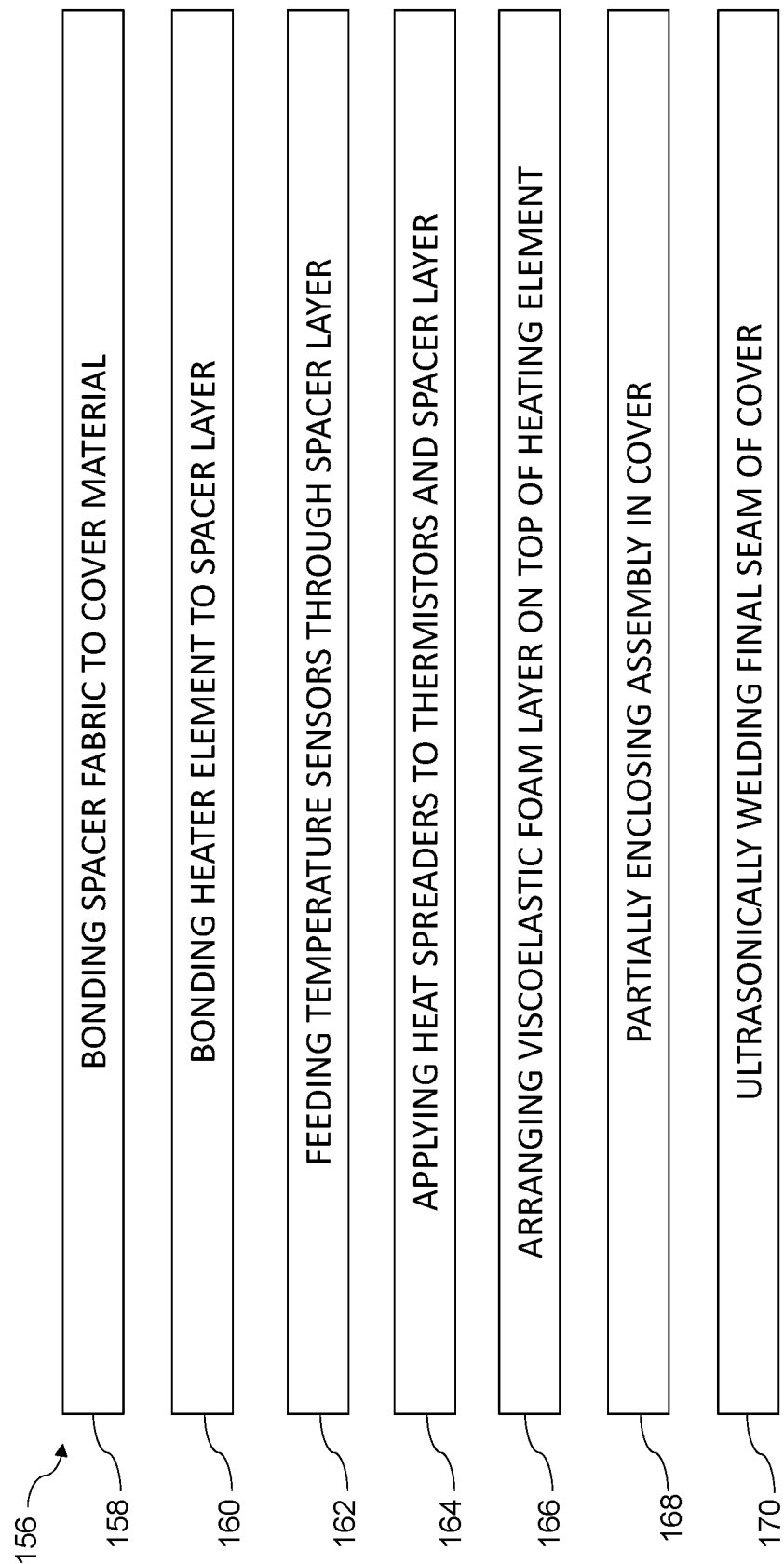
FIG. 20 is a flowchart showing an exemplary method of manufacturing the blanket of FIG. 17.

Referring now to FIG. 20, an exemplary method 156 of manufacturing the over-body blanket 200 (as shown in FIGS. 17-19) is shown. A step 158 of the method 156 includes ultrasonically welding the spacer layer 82 to the cover 78. Prior to welding, urethane tape may be applied between the spacer layer 82 and the cover 78 at the area to be ultrasonically welded. The cover 78 and spacer layer 82 may be ultrasonically welded only along the perimeter of two of the opposed edges of the spacer layer 82. The size of the cover material may be larger than the size of the spacer layer, such that it can be folded over to form the cover in a subsequent step. In other embodiments, the cover is formed from a single piece of material and is closed on three sides (e.g., two of the sides having been sealed via ultrasonic welding or stitching) prior to assembly of the blanket, and the cover is turned inside-out such that the spacer layer is bonded to an inside surface of the cover.

Step 160 of the method 156 includes bonding the heater element 30 to the fabric of the spacer layer 82. The bonding may be conducted using double-sided tape, adhesive, or any other suitable securing method. The heater element 30 and spacer layer 82 may be bonded only along the perimeter/edges of the heater element 30 and spacer layer 82. In other embodiments, the heater element and spacer layer may be bonded via a full surface bond.

Step 162 of the method 156 includes feeding the temperature sensor assembly 102 through the spacer layer 82.

Step 164 of the method 156 includes applying the heat spreaders 116 on top of the thermistors and to the spacer layer 82 with contact adhesive.

Step 166 of the method 156 includes arranging the viscoelastic foam layer 104 on top of the heating element 30. Step 166 may include perimeter bonding the viscoelastic foam layer 104 to the heater element 30 and/or to the spacer layer 82. The bonding may be conducted using double-sided tape, adhesive, or any other suitable securing method.

Step 168 includes partially enclosing the assembly within the cover. In some embodiments in which the cover material is not yet at least partially formed into the cover, the cover material may be folded over on to the foam layer and the side edges of the cover layer may be ultrasonically welded (or stitched). In embodiments in which the cover layer is partially formed, the cover 78 may be turned inside out so that the assembly is provided inside the cover 78. Step 168 may also in some embodiments include applying a contact adhesive to the perimeter of the foam layer 104. Step 168 may also include feeding the cord of the wiring assembly 103 through the cover and sealing the cable on the outside of the cover using the grommet (e.g., using glue).

Step 170 of the method 156 includes ultrasonically welding (or stitching) a final seam of the cover 78.

Figure 21:
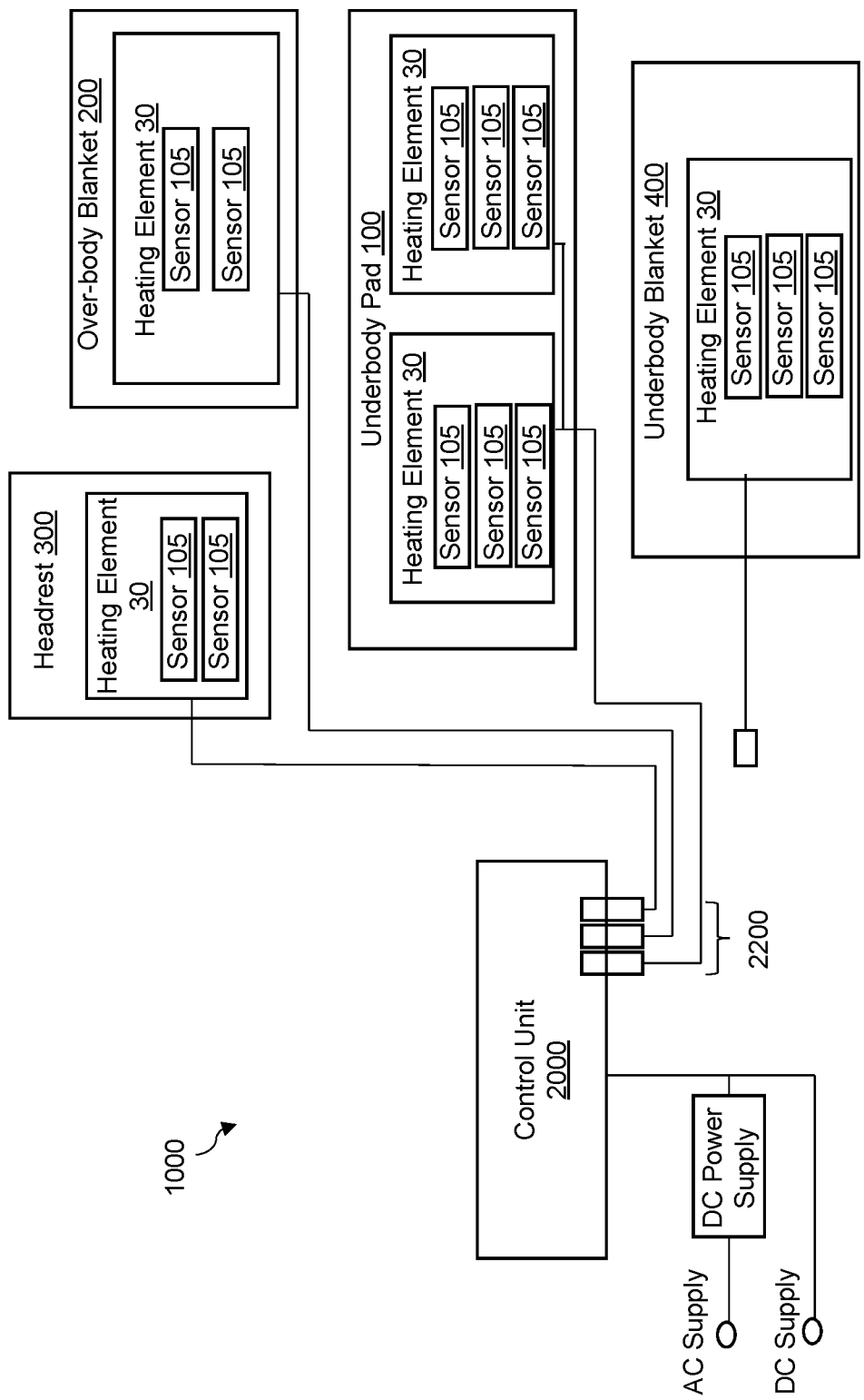
FIG. 21 is a schematic block diagram of an exemplary patient warming system.

FIG. 21 is a schematic block diagram of an exemplary patient warming system 1000. The patient warming system 1000 is a modular system, and includes a control unit 2000 that may be electrically coupled to one or more warming devices. The one or more warming devices may be controlled by the control unit 2000 to produce heat using one or more electrically resistive heating elements, and may provide conductive heat transfer from the heating accessory to the patient.

In the example shown, the control unit 2000 is electrically coupled to each of an underbody pad 100 (e.g., torso pad), over-body blanket 200, and headrest 300. In other embodiments, the control unit 200 may have more or fewer heating accessories electrically coupled thereto. A warming device used in connection with the patient warming system can be reusable or disposable (e.g., one-time use). In some embodiments, the warming devices used in the patient warming system are all reusable. In other embodiments, the warming devices used in the patient warming system are all disposable (e.g., one-time use). In other embodiments, the warming devices used in the patient warming system are a combination of reusable and disposable (e.g., one-time use) accessories. Other exemplary warming devices including one or more electrically resistive heating elements that may be coupled to the control unit 2000 and used in connection with the patient warming system 1000 include an underbody blanket 600 (shown in FIG. 1 as being in an uncoupled state), head pad (not shown), foot pad (not shown), and the like.

The patient warming system 1000 is modular in that any one of (or combination of) the warming devices may be coupled to the control unit 2000 (e.g., via the I/O interface 2220) and operated to provide conductive heat transfer to the patient. A coupled warming device may be uncoupled from the control unit 2000, and one or more other accessories may be electrically coupled to the control unit 2000 in its place. For example, FIG. 21 shows an underbody pad 100, overbody blanket 200, and headrest 300 coupled to the control unit 2000 via the I/O interface, and an underbody blanket 400 uncoupled from the control unit 2000. One of the warming devices (e.g., the underbody pad 100) may be uncoupled from the control unit 2000 and the underbody blanket 400 may be coupled to the control unit in its place.

It is noted that the exemplary embodiment of the underbody pad 100 shown in FIG. 21 includes two heating elements 30, each heating element having temperature sensors 105 associated therewith. As described above, one or more instances of the heating element 30 may be included in a warming device.

The control unit may support individual and/or concurrent operation of multiple heating accessories. In some embodiments, concurrent operation may be performed with the coupled heating accessories being controlled based on one or more common parameters (e.g., set point, on time, off time, etc.). In other embodiments, concurrent operation may be performed with the coupled heating accessories being controlled independently of one another. Adding, removing, or swapping a heating accessory may have no impact on the control of other accessories.

The control unit 2000 may be configured to control the temperature of all of the connected warming devices. The control unit 2000 may control application of power to the heating element(s) of a given connected warming device in accordance with the temperature setpoint and the temperature readings from a temperature sensor of the warming device. The control unit 2000 may also be configured to monitor temperature of the coupled warming devices and cut off the supply of power to one or more of the warming devices in the event that an over-temperature situation and/or fault is detected.

Although the invention has been shown and described with respect to certain preferred embodiments, it is understood that equivalents and modifications will occur to others skilled in the art upon the reading and understanding of the specification and the attached drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application. The present invention includes all such equivalents and modifications and is limited only by the scope of the following claims.

What is claimed is:

1. A heating element comprising:
   an electrically insulating layer;
   a resistive layer formed of a positive temperature coefficient material; and
   an electrically conductive layer disposed between the electrically insulating layer and the resistive layer and comprising a first bus and a second bus that is spaced apart from the first bus, wherein the first bus comprises a first bus base and first fingers that second fingers that extend from the second bus base toward the first bus base, the resistive layer electrically connecting the first bus and the second bus,
   wherein
   the electrically insulating layer, the electrically conductive layer, and the resistive layer are stacked to form a lamination and the lamination having a thickness and a width and length extending orthogonal to the thickness,
   the first bus base extends along a first side of the lamination in the width direction and the first fingers extend from the first bus base in the length direction toward the second bus base;
   the second bus base extends along a second side of the lamination opposite the first side in the width direction and the second fingers extend from the second bus base in the length direction toward the first bus base, the second fingers being interdigitated with the first fingers, and
   a plurality of slits extend through the lamination in the thickness direction and along the length direction between the first bus base and the second bus base, the slits segmenting the lamination into parallel strips that each have a width that is less than a length thereof, each strip including a plurality of the first fin ers a plurality of the second fingers interdigitated with the plurality of the first fingers, and the resistive layer.

2. The heating element according to claim 1, wherein the slits extend along more than half the length of the lamination.

3. The heating element according to claim 1, wherein the first fingers and the second fingers extend parallel to the slits.

4. The heating element according to claim 1, further comprising a first terminal connected to the first bus base and a second terminal connected to the second bus base, wherein the first terminal and the second terminal are arranged to provide a counter current flow pattern across the lamination.

5. The heating element according to claim 4, wherein the first terminal and the second terminal are diagonally opposed relative to each other across the lamination.

6. A warming device, comprising:
   the heating element according to claim 1;
   a spacer layer formed of a fabric material;
   a foam layer formed of a viscoelastic material;
   a temperature sensor assembly comprising a plurality of temperature sensors; and
   a cover material in which the lamination, the spacer layer, the viscoelastic foam layer, and the temperature sensor assembly are enclosed.

7. The warming device according to claim 6, further comprising a wiring assembly that is configured to provide voltage to the heating element and connects the thermistors to a control system.

8. The warming device according to claim 7, further comprising a grommet engageable against the cover material, wherein the grommet is configured to provide interference between a cord of the wiring assembly and the grommet.

9. The warming device according to claim 6, wherein the warming device is an underbody pad further comprising a base foam layer arrangement arranged adjacent the heating element opposite the spacer layer.

10. The warming device according to claim 6, wherein the warming device is a blanket in which the heating element is arranged between the spacer layer and the foam layer.

11. A warming device, comprising:
    a heating element comprising:

an electrically insulating layer;
a resistive layer formed of a positive temperature coefficient material; and
an electrically conductive layer disposed between the electrically insulating layer and the resistive layer and comprising a first bus and a second bus that is spaced apart from the first bus, the resistive layer electrically connecting the first bus and the second bus,
wherein the electrically insulating layer, the electrically conductive layer, and the resistive layer are stacked to form a lamination and the lamination having a thickness and a width and length extending orthogonal to the thickness, and the lamination has a plurality of slits extending through the thickness thereof and along a portion of the length thereof;
a spacer layer formed of a fabric material;
a foam layer formed of a viscoelastic material;
a temperature sensor assembly comprising a plurality of temperature sensors; and
a cover material in which the lamination, the spacer layer, the viscoelastic foam layer, and the temperature sensor assembly are enclosed,
wherein each temperature sensor comprises one or more thermistors and a heat spreader attached to the one or more thermistors, the heat spreader formed of a graphite material.

12. A warming device, comprising:
a heating element, comprising:
an electrically insulating layer;
a resistive layer formed of a positive temperature coefficient material; and
an electrically conductive layer disposed between the electrically insulating layer and the resistive layer and comprising a first bus and a second bus that is spaced apart from the first bus, the resistive layer electrically connecting the first bus and the second bus,
wherein the electrically insulating layer, the electrically conductive layer, and the resistive layer are stacked to form a lamination and the lamination having a thickness and a width and length extending orthogonal to the thickness;
a spacer layer formed of a fabric material;
a foam layer formed of a viscoelastic material;
a temperature sensor assembly comprising a plurality of temperature sensors; and
a cover material in which the lamination, the spacer layer, the viscoelastic foam layer, and the temperature sensor assembly are enclosed,
wherein each temperature sensor comprises one or more thermistors and a heat spreader attached to the one or more thermistors, the heat spreader formed of a graphite material and comprises a clover leaf shape.

13. The warming device according to claim 12 further comprising a wiring assembly that is configured to provide voltage to the heating element and connects the temperature sensors to a control system.

14. The warming device according to claim 13, further comprising a grommet engageable against the cover material, wherein the grommet is configured to provide interference between a cord of the wiring assembly and the grommet.

15. The warming device according to claim 12, wherein the warming device is a blanket in which the heating element is arranged between the spacer layer and the foam layer.

16. A warming device, comprising:
a heating element comprising:
an electrically insulating layer;
a resistive layer formed of a positive temperature coefficient materal; and
an electrically conductive layer disposed between the electrically insulating layer and the resistive layer and comprising a first bus and a second bus that is spaced apart from the first bus, the resistive layer electrically connecting the first bus and the second bus,
wherein the electrically insulating layer, the electrically conductive layer, and the resistive layer are stacked to form a lamination and the lamination having a thickness and a width and length extending orthogonal to the thickness;
a spacer layer formed of a fabric material;
a foam layer formed of a viscoelastic material;
a temperature sensor assembly comprising a plurality of temperature sensors; and
a cover material in which the lamination, the spacer layer, the viscoelastic foam layer, and the temperature sensor assembly are enclosed,
wherein the warming device is an underbody pad further comprising:
an additional spacer layer having a thickness that is less than a thickness of the spacer layer, wherein the spacer layer is arranged adjacent the heating element, the foam layer is arranged adjacent the spacer layer, and the additional spacer layer is arranged adjacent the foam layer opposite the spacer layer.

17. The warming device according to claim 16, further comprising a base foam layer arrangement that is arranged adjacent the heating element opposite the spacer layer and comprises a plurality of different foam layers.

* * * * *

UNITED STATES PATENT AND TRADEMARK OFFICE
CERTIFICATE OF CORRECTION

| | | |
|---|---|---|
| PATENT NO. | : 12,127,309 B2 | Page 1 of 1 |
| APPLICATION NO. | : 17/162298 | |
| DATED | : October 22, 2024 | |
| INVENTOR(S) | : Richard P. Nardo et al. | |

It is certified that error appears in the above-identified patent and that said Letters Patent is hereby corrected as shown below:

In the Claims

Claim 1, Column 23, Line 67, after "that" and before "second", insert -- extend from the first bus base and the second bus comprises a second bus base and --.

Claim 1, Column 24, Line 24, replace "fin ers" with -- fingers --.

Claim 16, Column 26, Line 20, replace "materal" with -- material --.

Signed and Sealed this
Eighteenth Day of February, 2025

Coke Morgan Stewart
*Acting Director of the United States Patent and Trademark Office*